United States Patent
Karapetian et al.

(10) Patent No.: US 9,198,649 B2
(45) Date of Patent: Dec. 1, 2015

(54) ROTATING LOCKING MEMBER SUTURE ANCHOR AND METHOD FOR SOFT TISSUE REPAIR

(75) Inventors: Emil Karapetian, Huntington Beach, CA (US); Steven Wolf, Mission Viejo, CA (US)

(73) Assignee: ArthroCare Corporation, Austin, TX (US)

( * ) Notice: Subject to any disclaimer, the term of this patent is extended or adjusted under 35 U.S.C. 154(b) by 379 days.

(21) Appl. No.: 13/359,631

(22) Filed: Jan. 27, 2012

(65) Prior Publication Data

US 2013/0197575 A1    Aug. 1, 2013

(51) Int. Cl.
*A61B 17/04*    (2006.01)

(52) U.S. Cl.
CPC ..... *A61B 17/0401* (2013.01); *A61B 2017/0409* (2013.01); *A61B 2017/0412* (2013.01); *A61B 2017/0422* (2013.01); *A61B 2017/0451* (2013.01); *A61B 2017/0496* (2013.01)

(58) Field of Classification Search
USPC ................ 606/232, 215; 24/170, 191, 134 R, 24/134 KB
See application file for complete search history.

(56) References Cited

U.S. PATENT DOCUMENTS

| | | | |
|---|---|---|---|
| 918,570 A | 4/1909 | Mather | 292/318 |
| 1,153,053 A | 9/1915 | Forster | 43/44.85 |
| 1,565,041 A | 12/1925 | Arneu | 24/129 R |
| 2,269,963 A | 1/1942 | Wrapler | 604/604 |
| 2,485,531 A | 10/1949 | Dzus et al. | 128/92 |
| 2,600,395 A | 6/1952 | Domoj et al. | 87/13 |
| 3,143,916 A | 8/1964 | Rice | 85/71 |
| 3,942,407 A | 3/1976 | Mortensen | 85/71 |
| 3,946,740 A | 3/1976 | Bassett | 128/334 |
| 3,994,521 A | 11/1976 | Van Gompel | 292/319 |
| 4,109,658 A | 8/1978 | Hughes | 128/340 |
| 4,210,148 A | 7/1980 | Stivala | 606/232 |
| 4,274,324 A | 6/1981 | Giannuzzi | 411/38 |
| 4,301,551 A | 11/1981 | Dore et al. | 623/13.3 |
| 4,319,428 A | 3/1982 | Fox | 47/42 |
| 4,345,601 A | 8/1982 | Fukuda | 128/339 |

(Continued)

FOREIGN PATENT DOCUMENTS

| | | | |
|---|---|---|---|
| DE | 3509417 | 9/1986 | A61B 17/58 |
| EP | 0 535 906 A2 | 4/1993 | A61B 17/04 |

(Continued)

OTHER PUBLICATIONS

PCT Search Report and Written Opinion for PCT/US06/20657) 7pgs, Mailed Oct. 2, 2007.

(Continued)

*Primary Examiner* — Tuan V Nguyen
(74) *Attorney, Agent, or Firm* — David A. Warmbold

(57) ABSTRACT

A suture anchor apparatus and method for anchoring a length of suture with respect to a target tissue has an anchor body with an anchoring structure for fixing the anchor body within the target tissue and a suture locking member. The moveable suture locking member is disposed at least partially within an anchor body lumen while a portion of the length of suture is looped around the suture locking member such that a first and second limb of suture exits the lumen. A suture locking member includes at least two elongate arms, and each arm has an extension dimension respectively, such that the first arm extension dimension is substantially greater than the second arm extension dimension.

30 Claims, 16 Drawing Sheets

(56) References Cited

U.S. PATENT DOCUMENTS

| | | | |
|---|---|---|---|
| 4,373,530 A | 2/1983 | Kilejian | 128/334 R |
| 4,384,389 A | 5/1983 | Sato | 24/136 K |
| 4,409,974 A | 10/1983 | Freedland | 128/92 |
| 4,456,270 A | 6/1984 | Zettl et al. | 279/62 |
| 4,467,478 A | 8/1984 | Jurgutis | 606/75 |
| 4,483,023 A | 11/1984 | Hoffman, Jr. et al. | 623/13.15 |
| 4,493,323 A | 1/1985 | Albright et al. | 128/340 |
| 4,580,936 A | 4/1986 | Francis et al. | 411/38 |
| 4,590,928 A | 5/1986 | Hunt et al. | 606/72 |
| 4,597,776 A | 7/1986 | Ullman et al. | 48/197 R |
| 4,605,414 A | 8/1986 | Czajka | 623/13.11 |
| 4,621,640 A | 11/1986 | Mulhollan et al. | 128/340 |
| 4,635,637 A | 1/1987 | Schreiber | 128/337 |
| 4,657,461 A | 4/1987 | Smith | 411/340 |
| 4,672,957 A | 6/1987 | Hourahane | 606/80 |
| 4,680,835 A | 7/1987 | Horng | 24/712.5 |
| 4,712,542 A | 12/1987 | Daniel et al. | 606/96 |
| 4,721,103 A | 1/1988 | Freedland | 128/92 |
| 4,731,084 A | 3/1988 | Dunn et al. | 623/13.19 |
| 4,738,255 A | 4/1988 | Goble et al. | 128/92 YF |
| 4,741,330 A | 5/1988 | Hayhurst | 123/43 R |
| 4,750,492 A | 6/1988 | Jacobs | 606/230 |
| 4,772,286 A | 9/1988 | Goble et al. | 623/13.14 |
| 4,779,616 A | 10/1988 | Johnson et al. | 606/148 |
| 4,809,408 A | 3/1989 | Abrahamson | 24/136 K |
| 4,823,780 A | 4/1989 | Odensten et al. | 606/96 |
| 4,828,439 A | 5/1989 | Giannuzzi | 411/37 |
| 4,851,005 A | 7/1989 | Hunt et al. | 623/18 |
| 4,870,957 A | 10/1989 | Goble et al. | 606/73 |
| 4,917,700 A | 4/1990 | Aikins | 623/13.19 |
| 4,926,860 A | 5/1990 | Stice et al. | 606/144 |
| 4,935,027 A | 6/1990 | Yoon | 606/146 |
| 4,946,467 A | 8/1990 | Ohi et al. | 606/228 |
| 4,946,468 A | 8/1990 | Li | 606/232 |
| 4,957,498 A | 9/1990 | Caspari | 606/146 |
| 4,968,315 A | 11/1990 | Gatturna | 606/72 |
| 4,981,149 A | 1/1991 | Yoon et al. | 128/898 |
| 4,987,665 A | 1/1991 | Dumican | 28/218 |
| 5,002,550 A | 3/1991 | Li | 606/139 |
| 5,019,093 A | 5/1991 | Kaplan et al. | 606/228 |
| 5,037,422 A | 8/1991 | Hayhurst | 606/72 |
| 5,046,513 A | 9/1991 | Gatturna | 128/898 |
| 5,059,201 A | 10/1991 | Asnis | 606/144 |
| 5,062,344 A | 11/1991 | Gerker | 87/8 |
| 5,085,661 A | 2/1992 | Moss | 606/139 |
| 5,147,166 A | 9/1992 | Harker | 411/29 |
| 5,195,542 A | 3/1993 | Gazielly et al. | 60/244 |
| 5,203,787 A | 4/1993 | Noblitt et al. | 606/232 |
| RE34,293 E | 6/1993 | Goble et al. | |
| 5,217,495 A | 6/1993 | Kaplan et al. | 623/13.18 |
| 5,219,359 A | 6/1993 | McQuilkin et al. | 606/232 |
| 5,224,946 A | 7/1993 | Hayhurst | 606/72 |
| 5,258,016 A | 11/1993 | DiPoto et al. | 606/232 |
| 5,263,984 A | 11/1993 | Li | 623/13.18 |
| 5,275,176 A | 1/1994 | Chandler | 606/242 |
| 5,304,184 A | 4/1994 | Hathaway et al. | 606/144 |
| 5,306,290 A | 4/1994 | Martins et al. | 606/232 |
| 5,324,308 A | 6/1994 | Pierce | 606/232 |
| 5,326,205 A | 7/1994 | Anspach, Jr. et al. | 411/43 |
| 5,330,442 A | 7/1994 | Green | 606/232 |
| 5,330,468 A | 7/1994 | Burkhart | 606/96 |
| 5,330,488 A | 7/1994 | Goldrath | 606/148 |
| 5,336,240 A | 8/1994 | Metzler | 606/232 |
| 5,354,298 A | 10/1994 | Lee et al. | 606/72 |
| 5,364,407 A | 11/1994 | Poll | 606/139 |
| 5,376,118 A | 12/1994 | Kaplan et al. | 623/23.72 |
| 5,383,905 A | 1/1995 | Golds et al. | 606/232 |
| 5,405,352 A | 4/1995 | Weston | 606/148 |
| 5,405,359 A | 4/1995 | Pierce | 606/232 |
| 5,411,523 A | 5/1995 | Goble | 606/232 |
| 5,413,579 A | 5/1995 | Tom Du | 606/87 |
| 5,417,691 A | 5/1995 | Hayhurst | 606/72 |
| 5,417,699 A | 5/1995 | Klein et al. | 606/139 |
| 5,417,712 A | 5/1995 | Whittaker et al. | 606/232 |
| 5,431,666 A | 7/1995 | Sauer et al. | 606/139 |
| 5,441,508 A | 8/1995 | Gazielly et al. | 606/151 |
| 5,445,167 A | 8/1995 | Yoon et al. | 128/898 |
| 5,450,860 A | 9/1995 | O'Connor | 606/224 |
| 5,454,823 A | 10/1995 | Richardson et al. | 606/148 |
| 5,464,427 A | 11/1995 | Curtis et al. | 606/232 |
| 5,470,335 A | 11/1995 | DuToit | 606/73 |
| 5,472,452 A | 12/1995 | Trott | 606/232 |
| 5,480,403 A | 1/1996 | Lee et al. | 606/72 |
| 5,486,197 A | 1/1996 | Le et al. | 606/232 |
| 5,499,991 A | 3/1996 | Garman et al. | 606/148 |
| 5,501,683 A | 3/1996 | Trott | 606/72 |
| 5,501,695 A | 3/1996 | Anspach, Jr. et al. | 606/72 |
| 5,505,735 A | 4/1996 | Li | 606/72 |
| 5,514,159 A | 5/1996 | Matula et al. | 606/232 |
| 5,520,700 A | 5/1996 | Beyar et al. | 606/139 |
| 5,522,820 A | 6/1996 | Caspari et al. | 606/148 |
| 5,527,322 A | 6/1996 | Klein et al. | 606/144 |
| 5,527,343 A | 6/1996 | Bonutti | 606/232 |
| 5,531,763 A | 7/1996 | Mastri et al. | 606/148 |
| 5,531,792 A | 7/1996 | Huene | 623/16 |
| 5,534,012 A | 7/1996 | Bonutti | 606/232 |
| 5,540,703 A | 7/1996 | Barker, Jr. et al. | 606/139 |
| 5,545,180 A | 8/1996 | Le et al. | 606/232 |
| 5,549,617 A | 8/1996 | Green et al. | 606/144 |
| 5,549,630 A | 8/1996 | Bonutti | 606/232 |
| 5,553,360 A | 9/1996 | Lucas et al. | 24/136 K |
| 5,562,689 A | 10/1996 | Green et al. | 606/151 |
| 5,569,305 A | 10/1996 | Bonutti | 606/232 |
| 5,569,306 A | 10/1996 | Thal | 606/232 |
| 5,571,104 A | 11/1996 | Li | 606/72 |
| 5,571,120 A | 11/1996 | Yoon | 606/148 |
| 5,573,540 A | 11/1996 | Yoon | 606/139 |
| 5,573,542 A | 11/1996 | Stevens | 606/144 |
| 5,573,548 A | 11/1996 | Nazre et al. | 606/232 |
| 5,575,801 A | 11/1996 | Habermeyer et al. | 606/148 |
| 5,584,835 A | 12/1996 | Greenfield | 606/73 |
| 5,584,839 A | 12/1996 | Gieringer | 606/96 |
| 5,584,860 A | 12/1996 | Goble et al. | 606/232 |
| 5,584,862 A | 12/1996 | Bonutti | 606/232 |
| 5,591,207 A | 1/1997 | Coleman | 606/232 |
| 5,593,189 A | 1/1997 | Little | 289/17 |
| 5,601,558 A | 2/1997 | Torrie et al. | 606/72 |
| 5,609,597 A | 3/1997 | Lehrer | 606/139 |
| 5,611,801 A | 3/1997 | Songer | 606/73 |
| 5,613,974 A | 3/1997 | Andreas et al. | 606/144 |
| 5,618,290 A | 4/1997 | Toy et al. | 606/139 |
| 5,618,314 A | 4/1997 | Harwin et al. | 606/232 |
| 5,626,614 A | 5/1997 | Hart | 606/232 |
| 5,630,824 A | 5/1997 | Hart | 606/139 |
| 5,632,748 A | 5/1997 | Beck, Jr. et al. | 606/72 |
| 5,645,589 A | 7/1997 | Li | 623/16 |
| 5,647,874 A | 7/1997 | Hayhurst | 606/72 |
| 5,649,940 A | 7/1997 | Hart et al. | 606/148 |
| 5,649,963 A | 7/1997 | McDevitt | 606/232 |
| 5,658,313 A | 8/1997 | Thal | 606/232 |
| 5,665,110 A | 9/1997 | Chervitz et al. | 606/232 |
| 5,665,112 A | 9/1997 | Thal | 606/232 |
| 5,667,528 A | 9/1997 | Colligan | 606/224 |
| D385,352 S | 10/1997 | Bales et al. | D24/145 |
| 5,681,333 A | 10/1997 | Burkhart et al. | 606/148 |
| 5,681,351 A | 10/1997 | Jamiolkowski | 606/232 |
| 5,683,418 A | 11/1997 | Luscombe et al. | 606/232 |
| 5,683,419 A | 11/1997 | Thai | 606/232 |
| 5,690,649 A | 11/1997 | Li | 606/139 |
| 5,693,060 A | 12/1997 | Martin | 606/148 |
| 5,697,950 A | 12/1997 | Fucci et al. | 606/232 |
| 5,702,397 A | 12/1997 | Goble et al. | 606/72 |
| 5,702,398 A | 12/1997 | Tarabishy | |
| 5,707,362 A | 1/1998 | Yoon | 604/164 |
| 5,707,394 A | 1/1998 | Miller et al. | 606/232 |
| 5,709,708 A | 1/1998 | Thal | 606/232 |
| 5,720,765 A | 2/1998 | Thal | 606/232 |
| 5,725,529 A | 3/1998 | Nicholson et al. | 606/72 |
| 5,725,541 A | 3/1998 | Anspach, III et al. | 606/151 |
| 5,728,136 A | 3/1998 | Thal | 606/232 |
| 5,733,307 A | 3/1998 | Dinsdale | 606/232 |
| 5,741,281 A | 4/1998 | Martin | 606/148 |
| 5,741,282 A | 4/1998 | Anspach, III et al. | 606/151 |
| 5,766,250 A | 6/1998 | Chervitz et al. | 623/13 |

(56) References Cited

U.S. PATENT DOCUMENTS

| | | | |
|---|---|---|---|
| 5,782,863 A | 7/1998 | Bartlett | 606/232 |
| 5,782,864 A | 7/1998 | Lizardi | 606/232 |
| 5,782,865 A | 7/1998 | Grotz | 606/72 |
| 5,791,899 A | 8/1998 | Sachdeva | 433/173 |
| 5,792,152 A | 8/1998 | Klein et al. | 606/144 |
| 5,797,927 A | 8/1998 | Yoon | 606/144 |
| 5,797,963 A | 8/1998 | McDevitt | 606/232 |
| 5,810,848 A | 9/1998 | Hayhurst | 606/144 |
| 5,810,854 A | 9/1998 | Beach | 606/232 |
| 5,814,052 A | 9/1998 | Nakao et al. | 606/148 |
| 5,814,071 A | 9/1998 | McDevitt et al. | 606/232 |
| 5,814,072 A | 9/1998 | Bonutti | 606/232 |
| 5,843,111 A | 12/1998 | Vijfvinkel | 606/171 |
| 5,849,004 A | 12/1998 | Bramlet | 606/232 |
| 5,860,978 A | 1/1999 | McDevitt | 606/72 |
| 5,860,991 A | 1/1999 | Klein et al. | 606/144 |
| 5,860,992 A | 1/1999 | Daniel et al. | 606/145 |
| 5,868,789 A | 2/1999 | Heubner | 606/232 |
| 5,879,372 A | 3/1999 | Bartlett | 606/232 |
| 5,882,340 A | 3/1999 | Yoon | 604/164 |
| 5,885,294 A | 3/1999 | Pedlick et al. | 606/80 |
| 5,891,168 A | 4/1999 | Thal | 606/232 |
| 5,893,850 A | 4/1999 | Cachia | 606/72 |
| 5,902,311 A | 5/1999 | Andreas et al. | 606/144 |
| 5,904,692 A | 5/1999 | Steckel et al. | 606/139 |
| 5,911,721 A | 6/1999 | Nicholson et al. | 606/72 |
| 5,921,994 A | 7/1999 | Andreas et al. | 606/144 |
| 5,935,107 A | 8/1999 | Taylor et al. | 604/164 |
| 5,935,129 A | 8/1999 | Mdevitt | 606/72 |
| 5,941,900 A | 8/1999 | Bonutti | 606/232 |
| 5,941,901 A | 8/1999 | Egan | 606/232 |
| 5,944,724 A | 8/1999 | Lizardi | 606/104 |
| 5,944,739 A | 8/1999 | Zlock et al. | 606/232 |
| 5,947,982 A | 9/1999 | Duran | 606/139 |
| 5,948,000 A | 9/1999 | Larsen et al. | 606/232 |
| 5,948,001 A | 9/1999 | Larsen | 606/232 |
| 5,948,002 A | 9/1999 | Bonutti | 606/232 |
| 5,957,953 A | 9/1999 | DiPoto et al. | 606/232 |
| 5,957,968 A | 9/1999 | Belden et al. | 607/126 |
| 5,961,530 A | 10/1999 | Moore et al. | 606/148 |
| 5,961,538 A | 10/1999 | Pedlick et al. | 606/232 |
| 5,968,044 A | 10/1999 | Nicholson et al. | 606/72 |
| 5,980,558 A | 11/1999 | Wiley | 606/232 |
| 5,980,559 A | 11/1999 | Bonutti | 606/232 |
| 5,984,933 A | 11/1999 | Yoon | 606/148 |
| 5,993,459 A | 11/1999 | Larsen | 606/104 |
| 6,001,104 A | 12/1999 | Benderev et al. | 606/80 |
| 6,001,109 A | 12/1999 | Kontos | 606/148 |
| 6,007,566 A | 12/1999 | Wenstrom | 606/232 |
| 6,007,567 A | 12/1999 | Bonutti | 606/232 |
| 6,010,525 A | 1/2000 | Bonutti et al. | 606/232 |
| 6,013,083 A | 1/2000 | Bennett | 606/104 |
| 6,017,346 A | 1/2000 | Grotz | 606/72 |
| 6,022,360 A | 2/2000 | Reimels et al. | 606/144 |
| 6,022,373 A | 2/2000 | Li | 606/232 |
| 6,024,758 A | 2/2000 | Thal | 606/232 |
| 6,033,430 A | 3/2000 | Bonutti | 606/232 |
| 6,036,699 A | 3/2000 | Andreas et al. | 606/139 |
| 6,045,571 A | 4/2000 | Hill et al. | 606/228 |
| 6,045,572 A | 4/2000 | Johnson et al. | 606/232 |
| 6,045,573 A | 4/2000 | Wenstrom et al. | 606/232 |
| 6,045,574 A | 4/2000 | Thal | 606/232 |
| 6,048,351 A | 4/2000 | Gordon et al. | 606/144 |
| 6,051,006 A | 4/2000 | Shluzas et al. | 606/148 |
| 6,053,935 A | 4/2000 | Brenneman et al. | 606/232 |
| 6,056,773 A | 5/2000 | Bonutti | 606/232 |
| 6,066,146 A | 5/2000 | Carroll et al. | 606/148 |
| 6,066,160 A | 5/2000 | Colvin et al. | 606/232 |
| 6,068,648 A | 5/2000 | Cole et al. | 606/232 |
| 6,086,608 A | 7/2000 | Elk et al. | 606/232 |
| 6,096,051 A | 8/2000 | Kortenbach et al. | 606/144 |
| 6,102,934 A | 8/2000 | Li | 606/232 |
| 6,117,160 A | 9/2000 | Bonutti | 606/215 |
| 6,117,161 A | 9/2000 | Li | 606/232 |
| 6,143,004 A | 11/2000 | Davis et al. | 606/144 |
| 6,146,386 A | 11/2000 | Blackman | 606/103 |
| 6,146,406 A | 11/2000 | Shluzas et al. | 606/232 |
| 6,149,669 A | 11/2000 | Li | 606/232 |
| 6,156,039 A | 12/2000 | Thai | 606/72 |
| 6,156,056 A | 12/2000 | Kearns et al. | 606/232 |
| 6,159,235 A | 12/2000 | Kim | 606/232 |
| 6,162,537 A | 12/2000 | Martin et al. | 428/373 |
| 6,171,317 B1 | 1/2001 | Jackson et al. | 606/148 |
| 6,200,329 B1 | 3/2001 | Fung et al. | 606/232 |
| 6,200,893 B1 | 3/2001 | Sneh | 438/685 |
| 6,206,895 B1 | 3/2001 | Levison | 606/144 |
| 6,217,592 B1 | 4/2001 | Freda et al. | 606/145 |
| 6,221,107 B1 | 4/2001 | Steiner et al. | 623/13.14 |
| 6,228,096 B1 | 5/2001 | Marchand | 606/139 |
| 6,241,736 B1 | 6/2001 | Sater | 606/104 |
| 6,267,766 B1 | 7/2001 | Burkhart | 606/72 |
| 6,280,474 B1 | 8/2001 | Cassidy et al. | 623/16.11 |
| 6,293,961 B2 | 9/2001 | Schwartz | 606/232 |
| 6,295,700 B1 * | 10/2001 | Plzak | 24/134 R |
| 6,315,781 B1 | 11/2001 | Reinhardt | 606/108 |
| 6,319,252 B1 | 11/2001 | McDevitt et al. | 606/60 |
| 6,319,269 B1 | 11/2001 | Li | 606/232 |
| 6,319,271 B1 | 11/2001 | Schwartz | 606/232 |
| 6,328,758 B1 | 12/2001 | Tornier et al. | 606/232 |
| 6,355,053 B1 | 3/2002 | Li | 606/232 |
| 6,409,743 B1 | 6/2002 | Fenton | 606/232 |
| 6,432,123 B2 | 8/2002 | Schwartz et al. | 606/232 |
| 6,436,109 B1 | 8/2002 | Kontes | 606/148 |
| 6,451,030 B2 | 9/2002 | Li et al. | 606/139 |
| 6,464,713 B2 | 10/2002 | Bonutti | 606/232 |
| 6,468,293 B2 | 10/2002 | Bonutti et al. | 606/232 |
| 6,471,715 B1 | 10/2002 | Weiss | 606/216 |
| 6,475,230 B1 | 11/2002 | Bonutti et al. | 606/232 |
| 6,491,714 B1 | 12/2002 | Bennett | 606/232 |
| 6,517,542 B1 | 2/2003 | Papay et al. | 606/73 |
| 6,520,980 B1 | 2/2003 | Foerster | 606/232 |
| 6,524,317 B1 | 2/2003 | Ritchart et al. | 606/72 |
| 6,527,794 B1 | 3/2003 | McDevitt et al. | 606/232 |
| 6,540,770 B1 | 4/2003 | Tornier et al. | 606/232 |
| 6,569,187 B1 | 5/2003 | Bonutti et al. | 606/232 |
| 6,575,987 B2 | 6/2003 | Gellman et al. | 606/151 |
| 6,582,453 B1 | 6/2003 | Tran et al. | 606/232 |
| 6,585,730 B1 | 7/2003 | Foerster | 606/232 |
| 6,635,073 B2 | 10/2003 | Bonutti | 606/232 |
| 6,638,279 B2 | 10/2003 | Bonutti | 606/60 |
| 6,645,227 B2 | 11/2003 | Fallin et al. | 606/232 |
| 6,648,903 B1 | 11/2003 | Pierson, III | 606/232 |
| 6,652,561 B1 | 11/2003 | Tran | 606/232 |
| 6,656,183 B2 | 12/2003 | Colleran et al. | 606/232 |
| 6,660,008 B1 | 12/2003 | Foerster et al. | 606/72 |
| 6,660,023 B2 | 12/2003 | McDevitt et al. | 606/232 |
| 6,673,094 B1 | 1/2004 | McDevitt et al. | 606/232 |
| 6,679,896 B2 | 1/2004 | Gellman et al. | 606/148 |
| 6,682,549 B2 | 1/2004 | Bartlett | 606/232 |
| 6,689,154 B2 | 2/2004 | Bartlett | 606/232 |
| 6,692,516 B2 | 2/2004 | West et al. | 606/232 |
| 6,736,829 B1 | 5/2004 | Li et al. | 606/232 |
| 6,770,076 B2 | 8/2004 | Foerster | 606/72 |
| 6,780,198 B1 | 8/2004 | Gregoire et al. | 606/232 |
| 6,855,157 B2 | 2/2005 | Foerster et al. | 606/232 |
| 6,860,887 B1 | 3/2005 | Frankie | 606/104 |
| 6,887,259 B2 | 5/2005 | Lizardi | 606/232 |
| 6,939,379 B2 | 9/2005 | Sklar | 623/13.14 |
| 6,972,027 B2 | 12/2005 | Fallin et al. | 606/232 |
| 7,083,638 B2 | 8/2006 | Foerster | 606/232 |
| 7,087,064 B1 | 8/2006 | Hyde | 606/142 |
| 7,090,690 B2 | 8/2006 | Foerster et al. | 606/232 |
| 7,104,999 B2 | 9/2006 | Overaker | 606/142 |
| 7,144,415 B2 | 12/2006 | Del Rio et al. | 606/232 |
| 7,150,750 B2 | 12/2006 | Damarati | 623/17.11 |
| 7,150,757 B2 | 12/2006 | Fallin et al. | 606/232 |
| 7,247,164 B1 | 7/2007 | Ritchart et al. | 606/232 |
| 7,320,701 B2 | 1/2008 | Haut et al. | 606/232 |
| 7,329,272 B2 | 2/2008 | Burkhart et al. | 606/232 |
| 7,381,213 B2 | 6/2008 | Lizardi | 606/232 |
| 7,410,489 B2 | 8/2008 | Dakin et al. | 606/103 |
| 7,556,640 B2 | 7/2009 | Foerster | 606/232 |
| 7,588,587 B2 | 9/2009 | Barbieri et al. | 606/232 |
| 7,615,061 B2 | 11/2009 | White et al. | 606/148 |

(56) References Cited

U.S. PATENT DOCUMENTS

| | | | |
|---|---|---|---|
| 7,637,926 B2 | 12/2009 | Foerster et al. | 606/232 |
| 7,674,274 B2 | 3/2010 | Foerster et al. | 606/232 |
| 7,682,374 B2 | 3/2010 | Foerster | 606/72 |
| 7,695,494 B2 | 4/2010 | Foerster | 606/232 |
| 7,837,710 B2 | 11/2010 | Lombardo et al. | 606/232 |
| 7,867,251 B2 | 1/2011 | Colleran et al. | 606/232 |
| 7,938,847 B2 | 5/2011 | Fanton et al. | 606/232 |
| 7,963,972 B2 | 6/2011 | Foerster et al. | 606/139 |
| 7,981,140 B2 | 7/2011 | Burkhart | 606/232 |
| 8,109,966 B2 | 2/2012 | Ritchart et al. | 606/232 |
| 8,133,258 B2 | 3/2012 | Foerster et al. | 606/232 |
| 8,317,829 B2 | 11/2012 | Foerster et al. | 606/232 |
| 8,425,536 B2 | 4/2013 | Foerster et al. | 606/232 |
| 8,444,672 B2 | 5/2013 | Foerster | 606/232 |
| 8,657,854 B2 | 2/2014 | Foerster et al. | 606/232 |
| 8,685,060 B2 | 4/2014 | Foerster | 606/232 |
| 2003/0105489 A1 | 6/2003 | Eichhorn et al. | 606/232 |
| 2003/0167062 A1 | 9/2003 | Gambale | 606/232 |
| 2003/0195563 A1 | 10/2003 | Foerster | 606/232 |
| 2003/0195564 A1 | 10/2003 | Tran et al. | 606/232 |
| 2004/0133239 A1* | 7/2004 | Singhatat | 606/232 |
| 2004/0138683 A1 | 7/2004 | Shelton et al. | 606/151 |
| 2004/0138706 A1 | 7/2004 | Abrams et al. | 606/232 |
| 2004/0153074 A1 | 8/2004 | Bojarski et al. | 606/232 |
| 2004/0236336 A1 | 11/2004 | Foerster et al. | 606/72 |
| 2005/0033364 A1 | 2/2005 | Gregoire et al. | 606/232 |
| 2005/0080455 A1 | 4/2005 | Schmieding et al. | 606/232 |
| 2005/0090827 A1 | 4/2005 | Gedebou | 606/72 |
| 2005/0273101 A1 | 12/2005 | Schumacher | 606/61 |
| 2005/0277986 A1 | 12/2005 | Foerster | 606/232 |
| 2006/0004364 A1 | 1/2006 | Green et al. | 606/72 |
| 2006/0074422 A1 | 4/2006 | Story et al. | 606/142 |
| 2006/0079904 A1 | 4/2006 | Thal | 606/72 |
| 2006/0106423 A1 | 5/2006 | Weisel et al. | 606/232 |
| 2006/0161159 A1 | 7/2006 | Dreyfuss et al. | 606/72 |
| 2006/0271060 A1 | 11/2006 | Gordon | 606/232 |
| 2006/0271105 A1 | 11/2006 | Foerster | 606/232 |
| 2006/0282081 A1 | 12/2006 | Fanton et al. | 606/232 |
| 2007/0142838 A1 | 6/2007 | Jordan | 606/75 |
| 2007/0156148 A1 | 7/2007 | Fanton et al. | 606/72 |
| 2007/0276437 A1 | 11/2007 | Call et al. | 606/232 |
| 2008/0051836 A1 | 2/2008 | Foerster et al. | 606/232 |
| 2008/0119849 A1 | 5/2008 | Beardsley et al. | 606/61 |
| 2008/0319478 A1 | 12/2008 | Foerster et al. | 606/148 |
| 2009/0069823 A1 | 3/2009 | Foerster et al. | 606/103 |
| 2009/0222040 A1 | 9/2009 | Foerster et al. | 606/232 |
| 2009/0222041 A1 | 9/2009 | Foerster et al. | 606/232 |
| 2009/0248068 A1 | 10/2009 | Lombardo et al. | 606/232 |
| 2010/0191283 A1 | 7/2010 | Foerster et al. | 606/232 |
| 2013/0060280 A1 | 3/2013 | Wolf et al. | 606/232 |
| 2013/0197576 A1 | 8/2013 | Catania et al. | 606/232 |
| 2013/0197577 A1 | 8/2013 | Wolf et al. | 606/232 |
| 2013/0197578 A1 | 8/2013 | Gregoire et al. | 606/232 |
| 2013/0197579 A1 | 8/2013 | Foerster et al. | 606/232 |
| 2013/0267998 A1 | 10/2013 | Vijay et al. | 606/232 |
| 2014/0207189 A1 | 7/2014 | Foerster et al. | 606/232 |

FOREIGN PATENT DOCUMENTS

| | | | | |
|---|---|---|---|---|
| EP | 0 571 686 A1 | 12/1993 | | A61B 2/08 |
| EP | 0 611 557 A2 | 8/1994 | | A61B 2/08 |
| EP | 1 072 234 A2 | 1/2001 | | A61F 2/08 |
| EP | 1 072 237 A1 | 1/2001 | | A61F 2/36 |
| FR | 2777442 | 10/1999 | | A61B 17/04 |
| FR | 2777447 | 10/1999 | | A61B 17/56 |
| JP | 2286468 | 11/1990 | | B62D 1/16 |
| JP | 8-52154 | 2/1996 | | A61B 17/56 |
| JP | 08-206121 | 8/1996 | | A61B 17/04 |
| JP | 11-502437 | 3/1999 | | A61B 17/58 |
| JP | 2000-225118 | 8/2000 | | A61B 17/04 |
| WO | 89/10096 | 11/1989 | | A61B 19/00 |
| WO | 91/06247 | 5/1991 | | A61B 17/00 |
| WO | 95/06439 | 3/1995 | | A61B 17/00 |
| WO | 95/025469 | 9/1995 | | A61B 17/04 |
| WO | 96/28118 | 9/1996 | | A61F 5/00 |
| WO | 97/20522 | 6/1997 | | A61F 2/08 |
| WO | 99/53843 | 10/1999 | | A61B 17/04 |
| WO | 99/53844 | 10/1999 | | A61B 17/04 |
| WO | 02/21997 | 3/2002 | | A61B 17/04 |
| WO | 03/020137 | 3/2003 | | A61B 17/02 |
| WO | 03/049620 | 6/2003 | | A61B 17/04 |

OTHER PUBLICATIONS

PCT Search Report and Written Opinion for PCT/US06/21125 6pgs, Mailed May 22, 2008.
PCT International Search Report for PCT/US01/21905 3pgs, Mailed Jan. 22, 2002.
PCT International Preliminary Examination Report for PCT/US01/21905 3pgs, Mailed Oct. 17, 2003.
PCT International Search Report for PCT/US01/17689 3pgs, Mailed Dec. 19, 2001.
PCT International Preliminary Examination Report for PCT/US01/17689 15pgs, Mailed Feb. 9, 2003.
PCT International Search Report for PCT/US02/17493 1pg, mailed Mar. 27, 2003.
PCT International Preliminary Examination Report for PCT/US02/17493 4pgs, Mailed Sep. 8, 2003.
PCT International Search Report for PCT/US02/41018 2pgs, mailed Jun. 5, 2003.
PCT International Preliminary Examination Report for PCT/US02/41018 3pgs, Mailed Feb. 22, 2004.
PCT International Search Report for PCT/US02/04231 1pg, Mailed Aug. 14, 2002.
PCT International Preliminary Examination Report for PCT/US02/04231 3pgs, Mailed Nov. 13, 2002.
PCT International Search Report for PCT/US03/35695 1 pg, Mailed Feb. 14, 2005.
PCT International Preliminary Examination Report for PCT/US03/35695 4pgs, Mailed Dec. 21, 2005.
EP Partial European Search Report for EP02742470 3pgs, Mailed Apr. 13, 2004.
EP Supplementary European Search Report for EP02742470 5pgs, Mailed Jul. 30, 2004.
EP Extended Search Report for EP09162639 4pgs, Mailed Oct. 28, 2009.
EP Supplementary European Search Report for EP02792506 3pgs, Mar. 24, 2010.
UK Search Report for GB 0816111.9 3pgs, Dec. 16, 2008.
European Search Report for EP 02734649 3pgs, Jan. 22, 2009.
PCT Search Report and Written Opinion for PCT/US13/33664 10pgs, Jun. 14, 2013.
DE Examination Report for DE 102008046561.5 11 pgs, Nov. 16, 2012.

* cited by examiner

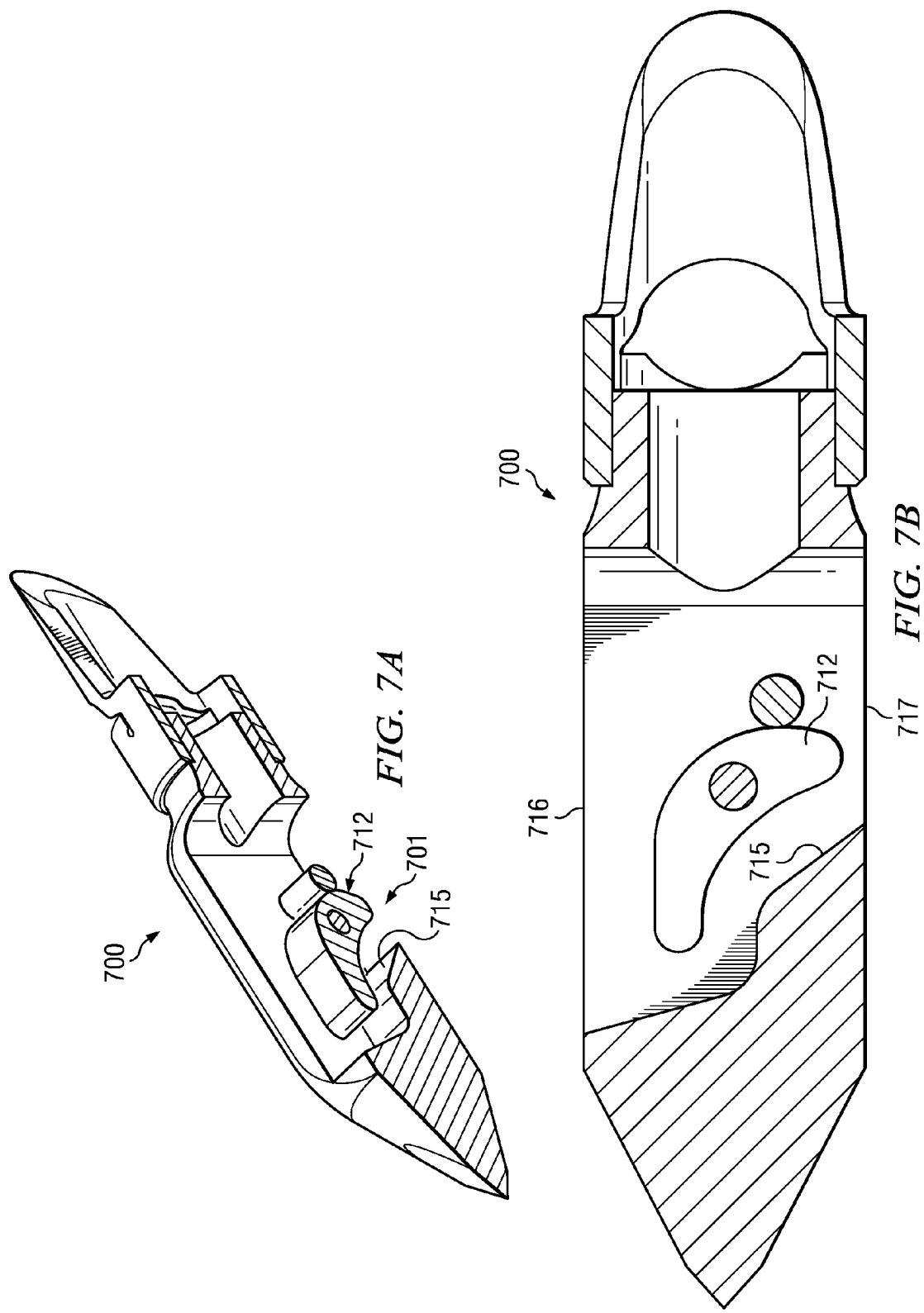

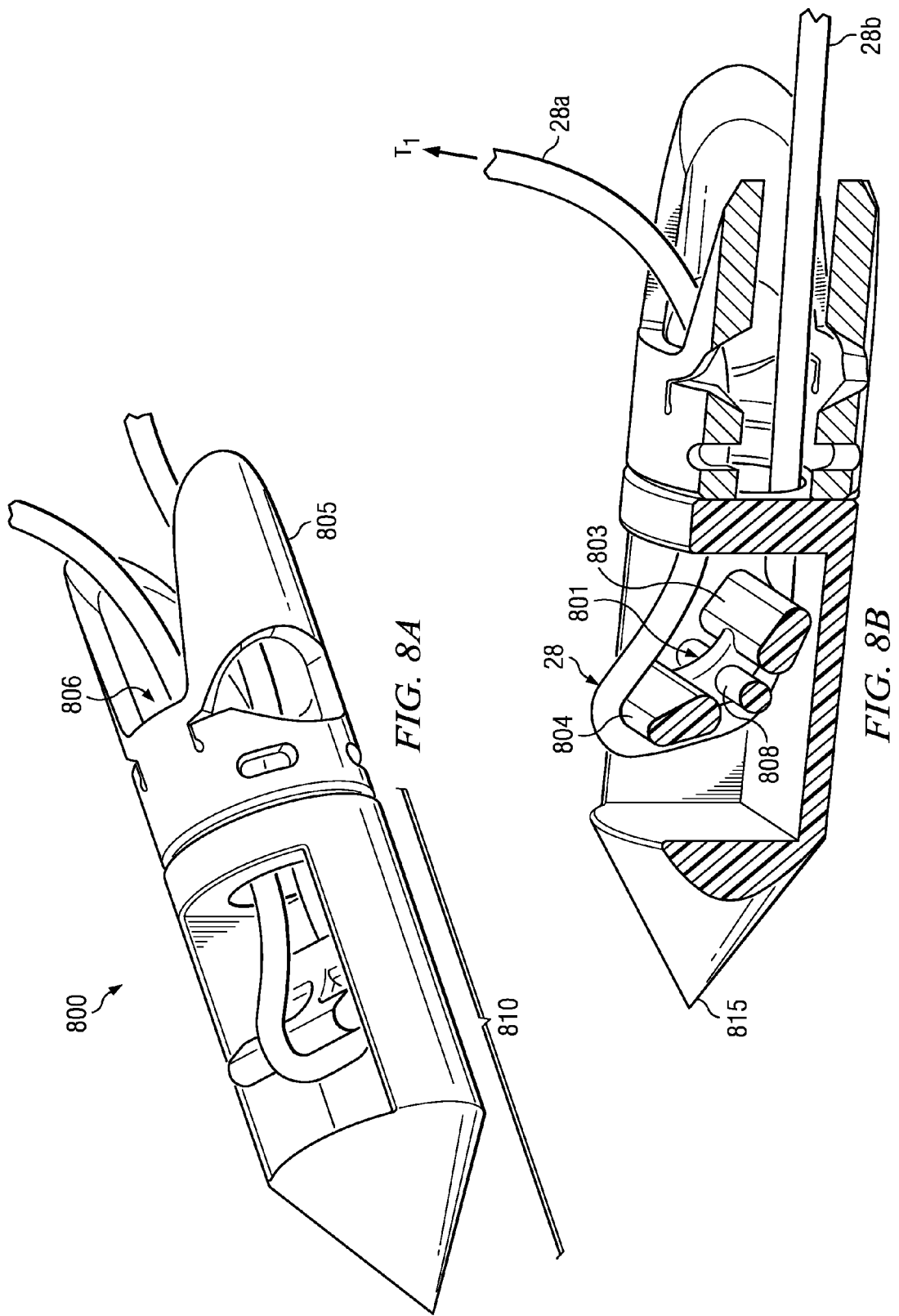

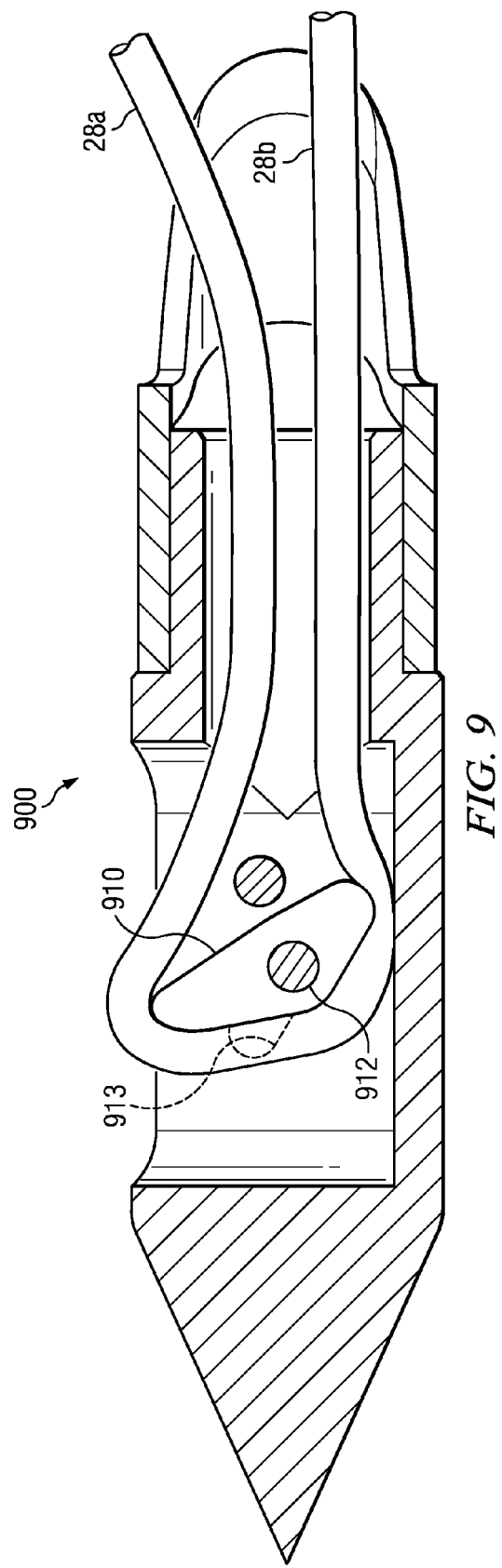

ROTATING LOCKING MEMBER SUTURE ANCHOR AND METHOD FOR SOFT TISSUE REPAIR

FIELD OF THE INVENTION

The present invention relates to apparatus and methods for repairing soft tissue regions. More particularly, the present invention relates to apparatus and methods for adjustably affixing torn soft tissues to a region of bone.

BACKGROUND

It is an increasingly common problem for tendons and other soft connective tissues to tear or to detach from associated bone. One such type of tear or detachment is a "rotator cuff" tear, wherein the supraspinatus tendon separates from the humerus, causing pain and loss of ability to elevate and rotate the arm. Complete separation of tissue from the bone can occur if the shoulder is subjected to gross trauma, but typically, the tear begins as a small lesion, especially in older patients.

To repair a torn rotator cuff, the typical course is to do so surgically, through a large incision. There are two types of open surgical approaches for repair of the rotator cuff, one known as the "classic open" and the other as the "mini-open". The classic open approach requires a large incision and complete detachment of the deltoid muscle from the acromion to facilitate exposure. The cuff is debrided to ensure suture attachment to viable tissue and to create a reasonable edge approximation. In addition, the humeral head is abraded or notched at the proposed soft tissue to bone reattachment point, as healing is enhanced on a raw bone surface. A series of small diameter holes, referred to as "transosseous tunnels", are "punched" through the bone laterally from the abraded or notched surface to a point on the outside surface of the greater tuberosity, commonly a distance of 2 to 3 cm. Finally, the cuff is sutured and secured to the bone by pulling the suture ends through the transosseous tunnels and tying them together using the bone between two successive tunnels as a bridge, after which the deltoid muscle must be surgically reattached to the acromion.

The mini-open technique differs from the classic approach by gaining access through a smaller incision and splitting rather than detaching the deltoid. Additionally, this procedure is typically performed in conjunction with arthroscopic acromial decompression. Once the deltoid is split, it is refracted to expose the rotator cuff tear. As before, the cuff is debrided, the humeral head is abraded, and the so-called "transosseous tunnels" are "punched" through the bone or suture anchors are inserted. Following the suturing of the rotator cuff to the humeral head, the split deltoid is surgically repaired.

Less invasive arthroscopic techniques continue to be developed in an effort to address the shortcomings of open surgical repair. Working through small trocar portals that minimize disruption of the deltoid muscle, surgeons have been able to reattach the rotator cuff using various suture anchor and suture configurations. The rotator cuff is sutured intracorporeally and an anchor is driven into bone at a location appropriate for repair. Rather than thread the suture through transosseous tunnels which are difficult or impossible to create arthroscopically using current techniques, the repair is completed by tying the cuff down against bone using the anchor and suture.

The skill level required to facilitate an entirely arthroscopic repair of the rotator cuff is fairly high. Intracorporeal suturing is clumsy and time consuming, and only the simplest stitch patterns can be utilized. Extracorporeal knot tying is somewhat less difficult, but the tightness of the knots is difficult to judge, and the tension cannot later be adjusted. Also, because of the use of suture anchors to provide a suture fixation point in the bone, the knots that secure the soft tissues to the anchor by necessity leave the knot bundle on top of the soft tissues. In the case of rotator cuff repair, this means that the knot bundle is left in the shoulder capsule where it can be felt by the patient postoperatively when the patient exercises the shoulder joint. So, knots tied arthroscopically are difficult to achieve, impossible to adjust, and are located in less than optimal areas of the shoulder. Suture tension is also impossible to measure and adjust once the knot has been fixed.

There are various suture anchor designs available for use by an orthopedic surgeon for attachment of soft tissues to bone. A number these designs include use of a locking plug which is forced into a cavity of the anchor body to secure the suture therein. Although there is some merit to this approach for eliminating the need for knots in the attachment of sutures to bone, a problem with being able to properly set the tension in the sutures exists. The user is required to pull on the sutures until appropriate tension is achieved, and then to set the plug portion into the suture anchor portion. This action increases the tension in the sutures, and may garrote the soft tissues or increase the tension in the sutures beyond the tensile strength of the material, breaking the sutures. In addition, the minimal surface area provided by this anchor design for pinching or locking the sutures in place will abrade or damage the suture such that the suture's ability to resist load will be greatly compromised. Additionally, once the suture is fixed, the suture cannot be adjusted or retensioned. This is a shortcoming of such designs because it is not uncommon for a physician to desire to reposition or adjust the tissue location and suture after the anchor has been set.

An example of a suture anchor that addresses some of the above mentioned shortcomings is shown in FIGS. 1A and 1B. Anchor 1 may include a rotatable or pivoting cam 5 to lock suture 28 within suture anchor 1. In this embodiment, suture leg 28a may be bound or connected to tissue (tissue not shown), and suture leg 28b may be free to be adjusted by the practitioner. In FIG. 1A, the bound suture tension (T1) is minimal as the tissue may not be adjacent the anchor 1, and the practitioner is applying open suture tension (T2) to draw the suture 28 around the cam 5 and essentially draw the tissue attached to bound suture leg 28a closer to the suture anchor 1 and into engagement with the bone. As the bound suture tension (T1) increases, due to the tissue being closer to its target location, T1 may begin to approximate or exceed the open suture tension (T2), and the resulting frictional force $F_{(T1+T2)}$ between the cam 5 and the suture 28 may cause the cam 5 to rotate clockwise, and clamp down and lock or wedge the suture 28 as shown in FIG. 1B. Problematically, as the coefficient of friction between the cam 5 and suture 28 decreases, the suture 28 may slip and cam 5 may not rotate or the lock force may not be sufficient, i.e. the lock mechanism may have a tendency to fail.

Thus, a suture anchor and method for repairing rotator cuff or fixing other soft tissues to a target bone tissue, wherein a lock mechanism provides more control to the user, allows the suture to be re-tensioned, maintains a strong locking force and functions reliably in a low friction environment is still desirable.

BRIEF SUMMARY

Described herein are apparatus, systems, and methods for repairing soft tissue. In some aspects of the invention, an apparatus affixes a first tissue region (e.g., a soft connective tissue) to a second tissue region (e.g., a bone) and allows for adjustment of the fixation between the tissue regions.

In one aspect of the invention, a suture anchor apparatus for anchoring a length of suture with respect to a target tissue is disclosed, including an anchor body with an anchoring structure for fixing the anchor body within the target tissue. The anchor body has a proximal end, a distal tip and at least one axial opening or internal lumen extending from the proximal end, distally into the anchor body. The anchor body also has a moveable suture locking member, disposed at least partially within the axial opening. A portion of the length of suture is looped around the suture locking member. This suture locking member includes at least two opposed elongate arms: a first torque arm and a second locking arm. Each elongate arm has a respective extension dimension where the torque arm extension dimension is substantially greater than the locking arm extension dimension. The suture locking member is moveable from an open position such that the length of suture may freely slide around the suture locking member, to a locked position where the length of suture is locked in position between a distal portion of the locking arm and a portion of the axial opening surface such that the suture may not slide anymore.

In some aspects of the invention, the suture locking member has a cam shape and the elongate arms extend radially from the cam rotational axis in approximately opposite directions from each other or approximately between 150 and 210 degrees from each other. Additionally the suture locking member may be manufactured from a low friction material and may have a low friction surface texture to improve the ability for the suture to slide and the cam to move.

In another aspect of the invention, a knotless suture anchor apparatus is disclosed for anchoring a length of suture with respect to a target tissue. This apparatus includes an anchor body with an anchoring structure for fixing the anchor body within the target bone, and the anchor body has a proximal end with an opening such that at least a first portion of suture may be inserted into the opening, extend distally and around a suture locking member located within the opening, such that a second portion of suture may then return proximally through the opening. The suture locking member has both a first arm and a second arm, each extending radially from a cam axis. A first portion of suture is in contact with and moves the first arm by applying a first tension to the first arm so that the first arm moves the suture locking member from an open position, where the length of suture may freely slide around the suture locking member, to a locked position where the length of suture may no longer slide freely. These arms are substantially opposed to one another.

In some further aspects of the invention, the second portion of suture may communicate with the second arm and move the suture locking member through the application of tension on the suture from a locked position to an open position wherein the length of suture may freely slide. In some aspects, when there are equivalent tensions on the first and second portions of suture, the resultant torque on the cam may move the cam to a locked position.

In some aspects of this invention, a method is disclosed for securing connective tissue to bone. This method includes the steps of securing a first limb of a length of suture to a portion of connective tissue to be attached to a portion of bone followed by threading a second limb of the length of suture through a lumen in a body of a suture anchor device and about a suture locking member disposed along the length of the lumen. The suture locking member may be moveably coupled to the suture anchor body and has a first elongate arm and a second elongate arm, wherein the first arm is substantially opposed to the second arm. The suture anchor device is then inserted into a portion of bone and an anchoring portion of the anchor is deployed to secure the suture anchor device in the surrounding bone. A driver portion may then be separated from the anchor and withdrawn from the patient's body. Tension is then applied to the second limb of the length of suture, such that the length of suture slides around the suture locking member and through a gap disposed between the second elongate arm and a wall in the lumen, so as to draw the first limb of the length of suture toward the suture anchor device, thereby securing the portion of connective tissue snugly to the portion of bone. Tension is then applied to the first limb of the length of suture so as to move the suture locking member to reduce the gap such that the length of suture is now no longer free to slide.

In some aspects of this invention, a further step may be taken to increase the gap once again and allow suture to freely move, involving increasing the tension applied to the second limb of the length of suture to move the suture locking member so as to increase the gap such that the soft tissue may be re-positioned relative to the portion of bone.

In another aspect of the invention, a method for operating a knotless suture anchor is described, including the steps of threading at least a first length of suture through a proximal end of a lumen in a body of a suture anchor device and about a suture locking member disposed along the length of the lumen such that a second length of suture exits the lumen proximal end. This suture locking member comprises an axis and at least a first and a second elongate arm. According to the method, any tension applied to the first length of suture is transferred to the first elongate arm and any tension applied by the second length of suture is transferred to the second elongate arm. The suture anchor device is then inserted into a portion of tissue and deployed to secure the device in surrounding tissue. A second tension is then applied to the second length of suture such that the length of suture slides freely around the suture locking member until the second tension becomes sufficient, at which point the suture locking member moves so as to fix the second length of suture in position.

In a further aspect of the invention, a suture anchor device for attaching connective tissue to bone is described. The anchor device includes an outer body, a lumen extending axially through the outer body and a suture locking or clamping member disposed within the lumen. This member has an axis of rotation and at least two elongate arms extending radially from the axis. A length of suture extends through this lumen and around a distal surface of the locking member, with the suture including a free end that extends proximally out of the suture anchor device. The suture also includes a bound end attached to soft tissue to be secured to bone. When the free end is placed in tension by a proximally directed force, the suture may travel about the suture clamping member until increased tension on the bound end causes the suture to move the suture clamping member. This movement causes an elongate arm to rotate closer to a lumen wall and to pinch a length of the suture, stopping any suture motion.

In a further aspect of the invention, a bone anchor system for attaching connective tissue to bone is disclosed. This system includes a distal suture anchor portion with an outer body having an outer surface, on which an outwardly deployable anchoring element is situated. This system also includes a proximal driver portion connected to the distal anchor portion at a proximal end thereof, the driver portion including an actuator for deploying the anchoring element outwardly, and the connection between the proximal driver portion and the distal anchor portion is releasable once the anchoring element has been deployed. The system also includes a suture clamping member movable within the anchor portion, and a length of suture disposed in proximity to the suture clamping member. The suture clamping member may have a rotatable cam member with two substantially opposed elongate arms, and the cam member is moveable from a first position to a second position. In the second position, one of the elongate arms compresses the length of suture against a portion of the suture anchor so as to lock the suture in position.

In a further aspect of the invention, an anchor apparatus for securing a length of suture with respect to a target tissue is disclosed, comprising an anchor body with an internal lumen and a rotatable suture locking member disposed within the lumen. The locking member has a connecting member and a first arm extending a first distance from the connecting member and a second arm extending a second distance from the connecting member and the first distance is substantially greater than the second distance. A portion of the length of suture is slidingly looped around the locking member such that a first and second suture free end exit an opening of the lumen, and when a first tension is applied to the first suture free end a torque is applied to the first arm, such that the locking member rotates to compress the length of suture between the second arm and the anchor body.

In another aspect of the invention, an anchor apparatus for securing a length of suture with respect to a target tissue is disclosed, comprising an anchor body with an internal lumen and a suture locking member disposed within the lumen. The suture locking member has a connecting member, connecting the suture locking member with the anchor apparatus, and a first arm extending a first distance from the connecting member and a second arm extending a second distance from the connecting member, and wherein the first distance is substantially greater than the second distance. A portion of the length of suture is slidingly looped around the suture locking member such that a first and second suture free end exit an opening of the lumen and this length of suture is compressed between the second arm and the anchor body when the locking member is moved from an open position to a locking position.

In another aspect of the invention, a method for securing a connective tissue to a portion of bone is disclosed, comprising the steps of fixing an anchor body within a portion of bone followed by the steps of securing a first limb of a length of suture to a portion of the connective tissue to be attached to the portion of the bone and then placing the length of suture distal to a suture locking member and inserting the suture locking member into a proximal lumen in the anchor body while simultaneously capturing the length of suture, such that the suture now loops around a distal surface of the suture locking member and exits and enters the lumen proximal end. The suture locking member is moveable and comprises a first elongate arm and a second elongate arm. Tension is then applied to the second limb of the length of suture, such that the length of suture slides around the suture locking member, so as to draw the first limb of the length of suture toward the anchor body, thereby positioning the portion of connective tissue snugly to the portion of bone. Tension may then be applied to the first limb of the length of suture so as to move the suture locking member such that the length of suture is compressed between the second elongate arm and the lumen.

A number of technical advantages are described herein. One potential technical advantage is that the suture anchor does not require a knot to be tied by the practitioner making the procedure potentially easier and quicker to complete. Another possible advantage is that the tension in the suture is adjustable, as the suture lock is reversible, allowing the practitioner to alter the suture tension as the procedure progresses. This may prevent needing supplemental securing means, wasting procedure time, and limiting the likelihood of any tissue tearing should the initial tension be set to high. An additional advantage is that the suture should easily slide around the low friction suture anchor and cam member when needed with minimal friction, but then lock in place once the practitioner wishes to do so. This will make for easy adjustability of the soft tissue with respect to the target bone. Additional advantages will be apparent to those of skill in the art and from the figures, description and claims provided herein.

BRIEF DESCRIPTION OF THE DRAWINGS

FIGS. 7A and 7B illustrate an alternative embodiment for a suture anchor with an alternative locking surface according to at least certain embodiments in the present disclosure;

FIGS. 8A and 8B illustrate an alternative embodiment for a suture anchor with a deformable locking cam according to at least certain embodiments in the present disclosure;

FIG. 9 illustrates an alternative embodiment for a suture anchor with a locking cam having a rotating and a sliding motion according to at least certain embodiments in the present disclosure;

DETAILED DESCRIPTION

Figure 1A:
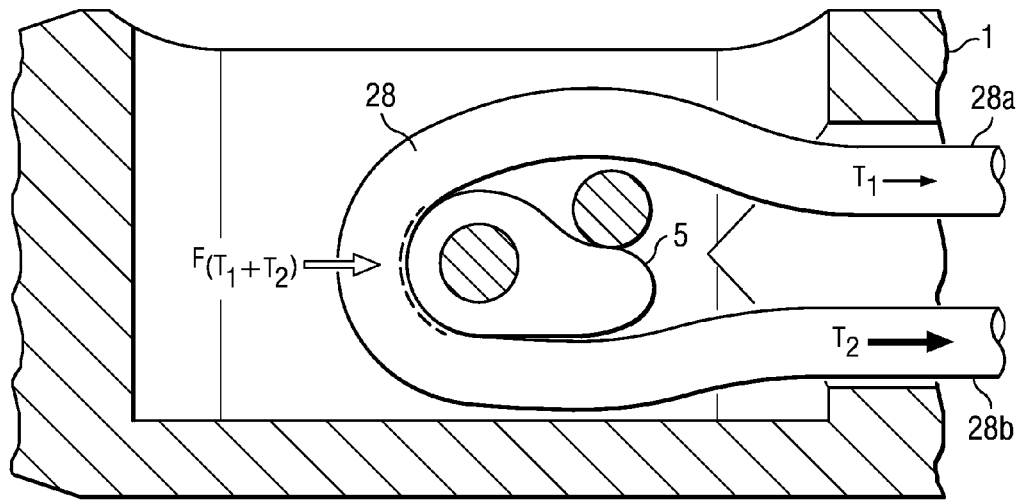
FIGS. 1A and 1B show an example of a suture anchor in an unlocked and locked position respectively.

Before the present invention is described in detail, it is to be understood that this invention is not limited to particular variations set forth herein as various changes or modifications may be made to the invention described and equivalents may be substituted without departing from the spirit and scope of the invention. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, many modifications may be made to adapt a particular situation, material, composition of matter, process, process act(s) or step(s) to the objective(s), spirit or scope of the present invention. All such modifications are intended to be within the scope of the claims made herein.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail).

The following co-pending patent applications, which are being submitted contemporaneously with the present application, are incorporated by reference in their entirety: U.S. Ser. No. 13/359,642, entitled "FREE FLOATING WEDGE SUTURE ANCHOR FOR SOFT TISSUE REPAIR"; U.S. Ser. No. 13/359,673, entitled "RESTRICTED WEDGE SUTURE ANCHOR AND METHOD FOR SOFT TISSUE REPAIR"; U.S. Ser. No. 13/359,826, entitled "BIASED WEDGE SUTURE ANCHOR AND METHOD FOR SOFT TISSUE REPAIR"; and U.S. Ser. No. 13/359,891, entitled "METHOD FOR SOFT TISSUE REPAIR WITH FREE FLOATING SUTURE LOCKING MEMBER", all of which are filed the same date as the present application, and all of which are commonly assigned to ArthroCare Corporation.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. It is also to be appreciated that unless defined otherwise, all technical and scientific terms used herein have the same meaning as commonly understood by one of ordinary skill in the art to which this invention belongs.

The present invention provides an improved knotless suture anchor apparatus for anchoring a length of suture with respect to a tissue structure. In an exemplary embodiment described herein, the apparatus is used to anchor a length of suture to the humeral bone of the human shoulder. The length of suture is desirably looped through soft tissue, such as a rotator cuff tendon, to approximate and fix the soft tissue with respect to the bone structure. It should be understood, however, that the suture anchor apparatus may be utilized to secure a length of suture to anatomies other than in a bone structure. In this regard, the preferred apparatus includes an anchor body within which the length of suture may be adjusted freely and then anchored or secured without knots. If the anchor body is to be implanted within a body tissue, structure on the anchor's exterior may be provided for securing it therein. In a preferred embodiment, the anchor body is inserted within a bone structure, and a pair of wings are deployed from the exterior of the anchor body to hold it within the cavity.

As mentioned, the present invention is particularly well-suited for repairing rotator cuff injuries by re-attaching the rotator cuff tendon to the outside of the humeral head. The invention permits minimally invasive surgeries on such injuries and greatly facilitates rapid and secure fixation of the rotator cuff tendon to the humeral head. It should be understood that the same principles described herein apply to the repair of other injuries in which soft tissue is to be re-attached to another tissue.

Embodiments of the present invention permit the user to insert at least one anchor into bone independently of any other anchor, lock an anchor in the bone, allow the user to subsequently tension or loosen a length of suture or wire between the anchors or between the anchor and soft tissue, to affix the soft tissue, immobilize the suture or wire, release and retension the suture, and then disassociate the inserter assembly from the at least one anchor, leaving the at least one anchor and the soft tissue repaired. Such an anchor inserter assembly may preferably eliminate the need to separately pass suture or wire, eliminate the need to tie knots, allow the procedure to be performed without the need to move an arthroscope from an articular side to a bursal side of the cuff, and by virtue of the small diameter of the anchor implants, reduce the size of the hole placed in any tissue, if passing the implant through.

Anchor Structure Overview

Figure 2A:
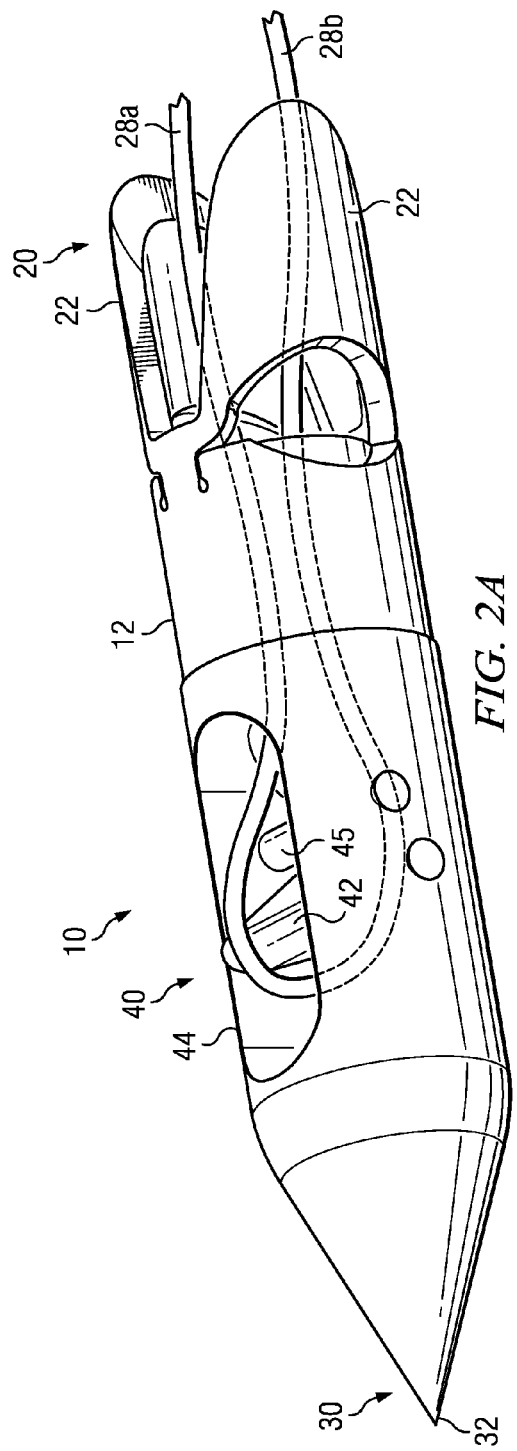
FIG. 2A shows a suture anchor with an adjustable suture locking member lock according to at least certain embodiments in the present disclosure.
Figure 2B:
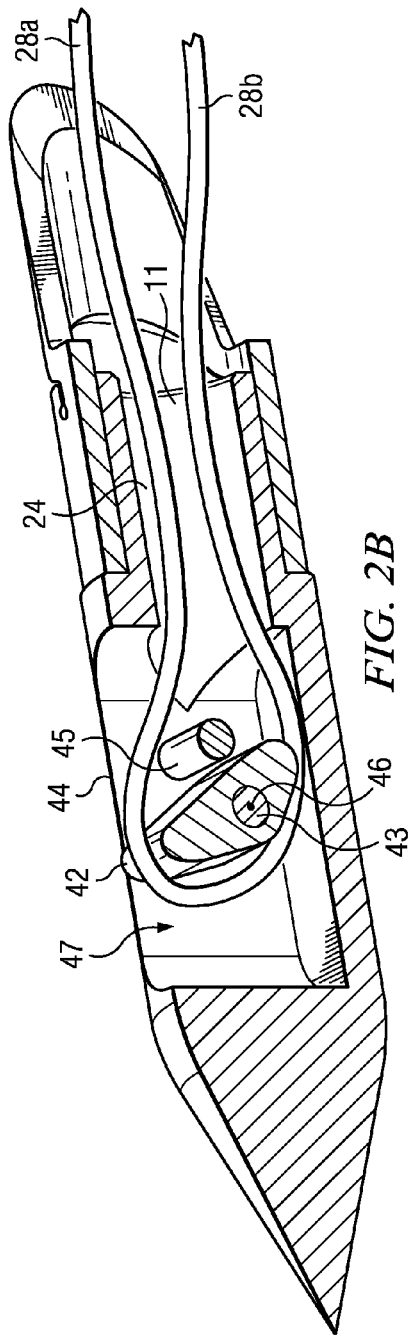
FIG. 2B shows a suture anchor with a camming suture lock with a longitudinal portion removed to show the cam member detail, according to at least certain embodiments in the present disclosure.

FIGS. 2A and 2B illustrate a suture anchor 10 including a body 12 having a proximal end 20, distal end 30 and suture locking portion 40 therebetween. Suture anchor 10 may generally have a smooth outer surface 12 for smooth and atraumatic insertion into a target tissue such as bone, and a portion of the suture anchor 10 may assume a larger profile and become locked in the wall of the target tissue (not shown) using a variety of anchoring means such as expansion ribs, molybolts, rivets, and other mechanisms. Alternate embodiments may include traumatic insertion such as a threaded or barbed portion on the outer surface 12 to lock into the wall of the target tissue (not shown). Shown here, proximal end 20 may include an anchoring element with two deformable wings 22 that may be permanently or reversibly deformed or outwardly deployable to have a larger profile so as to anchor or fix the suture anchor 10 within the target tissue. Suture anchor distal end 30 may comprise a piercing tip 32 configured to atraumatically pierce soft tissue and be driven into and through tissue and bone. Piercing tip 32 may be hollow or solid depending on strength or weight requirements and manufacturing technique. Anchor 10 may be preferably fabricated from a metal such as 316L stainless steel, although other materials such as titanium may be used. Alternative embodiments may include a blunted tip for inserting into a prepared bone passage or a threaded or tissue cutting tip.

Suture anchor 10 may also comprise an axial lumen or axial opening 24 which has a proximal aperture or opening 11 adjacent the anchoring element such as the deformable wings 22. Proximal opening 11 extends axially and distally through a portion of the anchor 10. At least one suture 28 which includes at least one bound leg 28a may be threaded through the opening 11 and may extend distally through the lumen 24, around the suture clamping member 42, and may subsequently be redirected proximally back through the lumen 24 and out of opening 11 to result in a free leg 28b. The bound limb, end, or leg 28a is considered bound because in practice, this leg of the suture is "bound" to the soft or connective tissues to be attached to the target tissue such as bone by virtue of passing the sutures through the connective or soft tissues using conventional suturing techniques known in the art. The free limb, end, or leg 28b is considered "free" because the surgeon or practitioner, in practice, has control over this leg of the suture with his or her hands or appropriate instrumentation.

Suture locking portion 40 may be a continuation or distal portion of lumen 24, and may be of similar size or diameter to lumen 24. Alternatively, suture locking portion 40 may be larger in dimension (i.e., length and diameter) than the proximal portion of the lumen 24 to allow the locking member 42 to move or pivot and function as intended, which will be described in further detail in later figures. Shown here, suture locking portion 40 comprises a chamber 47 that is in communication with distal end of lumen 24 so as to provide a continuous conduit for the suture routing described earlier. Suture locking portion 40 may also have at least one superior aperture 44, which interrupts the anchor outer surface 12, to allow rotational motion of locking member 42, when the suture bound end 28a is under tension. Aperture 44 may be an elongate shape and at least as wide as a portion of locking member 42 so as to provide a conduit or path for a portion of locking member to exit chamber 47 and be located outside (or outboard) of the suture anchor 10, when the locking member 42 is rotated clockwise so as to lock suture 28. Alternative embodiments of a suture locking portion 40 may have an inferior aperture on the opposite or inferior side of anchor 10 (not shown).

A suture locking member 42 is shown in FIGS. 2A and 2B, and is pivotally connected within anchor 10 using any suitable means or connecting members, such as a pivoting pin 43, which may be disposed approximately perpendicular to anchor longitudinal axis or lumen longitudinal axis. Pivoting pin 43 is characterized by an axis 46 and may intersect the longitudinal axis of anchor 10 and may be disposed approximately central to chamber 47. Placement of this pivoting pin 43 and therefore cam axis 46 affects the suture cam 42 operation, as will be described in later figures. Suture locking portion 40 may also include a stop 45, disposed approximately perpendicular to the anchor longitudinal axis, and extending through at least a portion of the chamber 47. Stop 45 may be of any shape, location or size operable to limit the rotational motion of suture cam 42 but not interfere with the sliding suture motion. As described in more detail herein, suture locking member 42 is operable to allow suture free leg 28b to be pulled so that the suture may slide freely around suture locking member 42 and into, out of, and through suture locking portion 40 so as to pull soft tissue attached to the bound leg 28a closer to suture anchor 10.

Once a sufficient amount of tension arises on the tissue bound leg 28a as a result of tissue approximation (or from the surgeon pulling on the bound leg), the suture locking member 42 is caused to rotate, and pinch the suture against a locking surface in the anchor body as will be described in more detail herein.

Suture locking member 42 may be preferably formed from a relatively low friction material, so as to allow easy sliding of the suture and may be formed from materials including a low friction UHMWPE such as MagnumWire® suture or Force Fiber. Suture locking member 42 may preferably have a smooth surface, and more specifically a smooth distal surface, to allow for easy suture sliding around the cam surface, during use. Suture locking member 42 may also have an elongate nest or groove (not shown) around the circumference or edge of locking member 42 to provide some limitation to any lateral motion of the suture 28 (e.g., to keep the suture 28 from slipping off). Suture 28 may also preferably comprise a low friction material such as polyester suture to create an overall low friction environment.

Suture Locking Detail

Figure 3A:
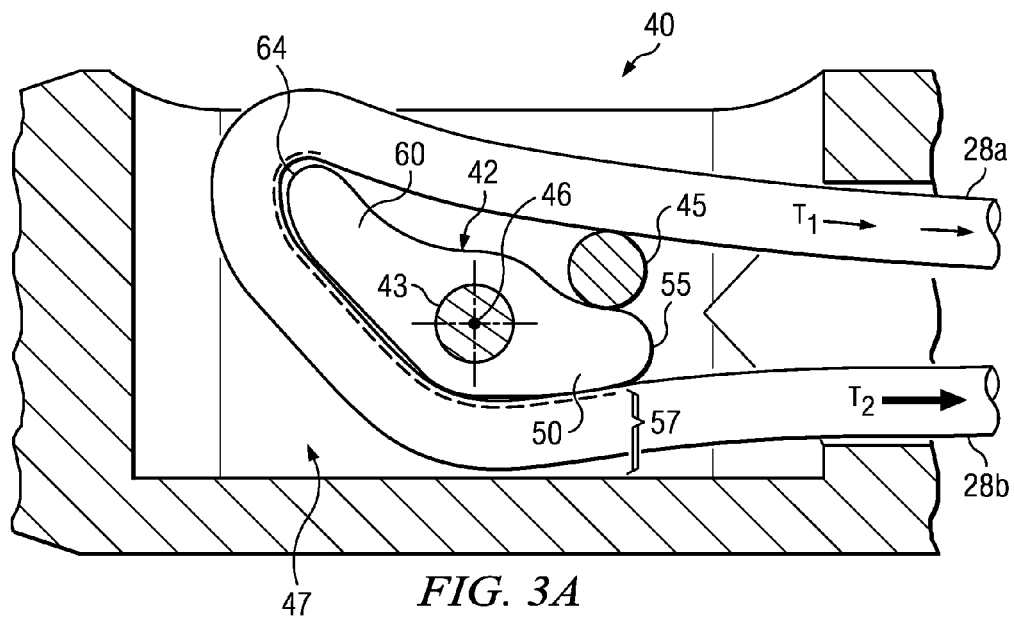
FIGS. 3A and 3B show a suture locking member mechanism in an open position and locked position respectively, according to at least certain embodiments in the present disclosure.

FIG. 3A is a representation of suture locking member or cam 42 according to at least certain embodiments described in the disclosure. Suture locking member 42 is shown in the open or unlocked position in FIG. 3A, with suture 28a and 28b free to move or slide within chamber 47 and around suture locking member 42. Suture locking member 42 has rotational axis 46, and may be rotationally coupled with pivot pin 43, so that suture locking member 42 may rotate freely about said pin 43. Pin 43 may be fixedly connected with suture anchor 10 and cam 42 may be biased or spring loaded (not shown here). Additional structures for holding the locking member in position or biasing the suture locking member are described in U.S. Ser. No. 13/359,826, filed Jan. 27, 2012, and entitled "Biased Wedge Suture Anchor and Method for Soft Tissue Repair".

Figure 3B:
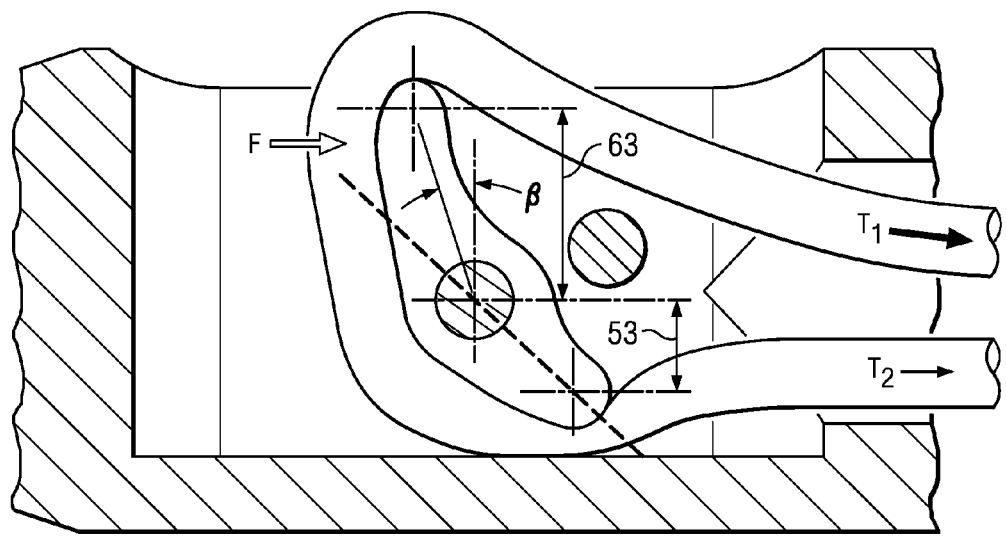
Figure 3C:
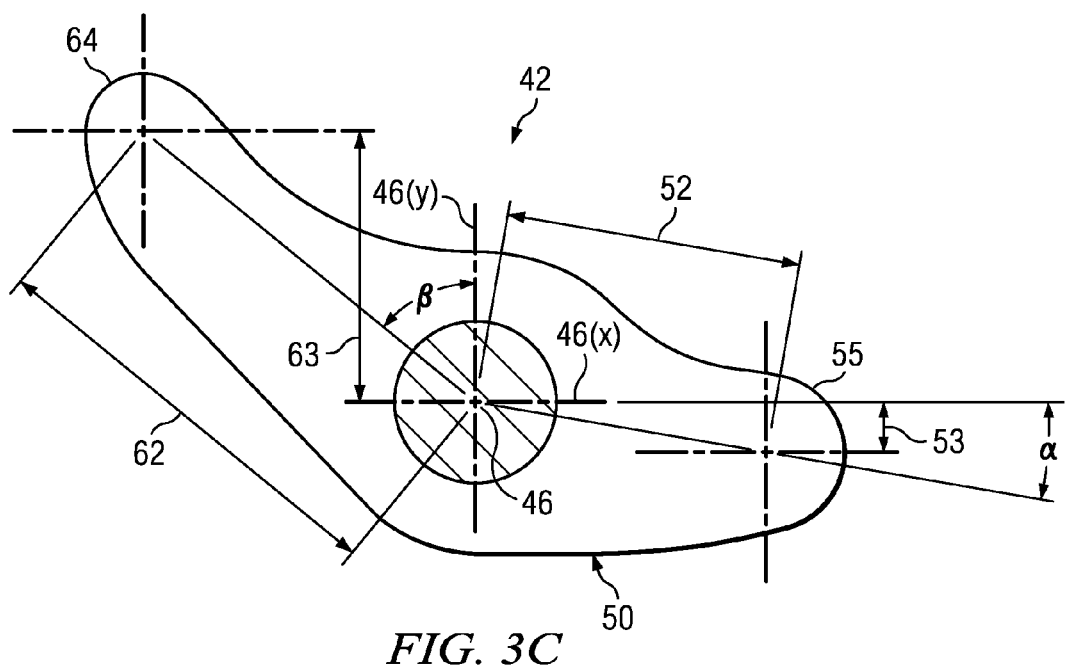
FIG. 3C shows a diagram of the locking member dimensions referenced in the specification.

Now, with reference to FIGS. 3A, 3B and 3C, the details of the operation of suture locking member 42 will follow, according to the embodiment described in FIGS. 2A and 2B. Suture locking member 42 may be characterized by two opposing elongate arms (50, 60) extending approximately radially from the axis 46, in substantially opposing directions, including a locking arm 50 and a torque arm 60. Although the suture locking member is shown having a cam shape, the shape of the suture locking member may vary. Exemplary shapes include without limitation a wedge, rocker, kidney, arcuate and plate.

While positioning a tissue connected with bound leg 28a, a tension (T2) may be applied to suture free end 28b, so that the locking member 42 is in the open position as shown in FIG. 3A such that the practitioner may slidingly draw suture 28 around cam 42. In this open position, locking arm 50 may be in contact with stop 45 as shown, so as to limit rotation of cam 42. When locking arm 50 is in contact with stop 45, there is a sufficient space or a gap 57 to allow for axial movement of suture. Specifically, space 57 should provide enough clearance for a suture of particular diameter to pass freely through the anchor body. Space 57 may be formed by the relative positions and sizes of chamber 47, stop 45, pin 43 and locking arm 50. For example, the positions of pin 43 and stop 45 relative to the walls of chamber 47 will dictate the dimension and clearance associated with space 57. Locking arm 50 has a locking arm extension 52, disposed at an angle α to the longitudinal axis of the suture anchor 10. This angle α is also relative to the direction that suture tension is applied. The angle α and locking arm extension 52 provides a calculateable locking arm perpendicular extension 53, also shown with an end point through the center point of tip 55. Extensions 52, 53 are represented for simplification purposes as extending from the axis 46 up to the center point of a circular tip 55. The exact dimensions of extensions 52, 53 may be more accurately described (but not shown here) as extending to an effective point of contact between, for example, the locking arm 50 and suture 28 and hence, the effective point where tension from the suture 28 is applied in the form of a force or torque on the cam. This exact dimension or distance therefore varies as the cam 42 rotates and also according to the tip 55 form. For simplification purposes, the center point of the tip 55 has been chosen, as these extensions 52, 53 shown are directly related to the effective extension dimensions. The same simplification is used for any torque arm extensions, which will be referenced below.

Torque arm 60 has a torque arm extension 62 and torque arm perpendicular extension 63 from the cam axis 46(x). Torque arm extension 62 as well as perpendicular extension 63, formed though the extension 62 and angle β, may be appreciably larger in dimension than locking arm extension 52 and locking arm perpendicular extension 53 respectively. As described above, extensions 62, 63 extend to an effective point of contact between torque arm 60 and suture 28, the point of contact being where torque is applied by the suture 28 to cam 42. Torque arm 60 and locking arm 50 both have rounded tips 64 and 55 respectively, so that suture will freely slide around cam 42. These tips 55, 64, may be circular, parabolic or elliptical in shape, and may preferably have no corners or sharp edges, so as not to snag or prevent free sliding motion of suture 28 around cam 42.

FIG. 3B shows a representation of the suture locking member 42 in a locked position, according to at least certain embodiments of the present disclosure. Suture 28 is shown locked or wedged against an inner inferior surface of chamber 47 or distal portion of the anchor lumen by locking arm 50, and more specifically by the distal portion or tip of locking arm 50, as gap 57 has been reduced via the motion of cam 42. In alternative configurations, suture 28 may be locked by clamping the locking arm 50 against pins or wedging features adjacent the suture cam 42 or against an alternative surface such as the distal surface of the chamber 47. Rotation of the cam 42 in a clockwise direction to lock the suture 28 may be achieved through sufficient tension from the bound leg 28a (T1). This tension is desirably sufficient to overcome opposing torque generated from suture free leg tension 28b (T2), so as to result in a net locking or clockwise torque on the torque arm 60. Because torque arm 60 perpendicular extension 63 is appreciably larger in dimension than locking arm perpendicular extension 53, once any tension (T1) from the suture bound leg 28a reaches a calculate-able portion of the tension (T2), or it approximates or is larger than the tension (T2), the resultant effect of these tensions (T1 and T2) will apply a net torque (F) on the cam 42 to rotate the cam 42 clockwise, via the nature of mechanical advantage resulting from the loaded torque arm on a rotatable member, to lock suture 28 in position. Using a mathematical representation, cam 42 may rotate to lock suture 28 once T1 has reached a value approximately equal to or larger than the following proportion of Tension T2:

$$\frac{\text{Locking Arm Perpendicular extension 53}}{\text{Torque Arm perpendicular extention 63}} \times T2$$

Figure 1B:
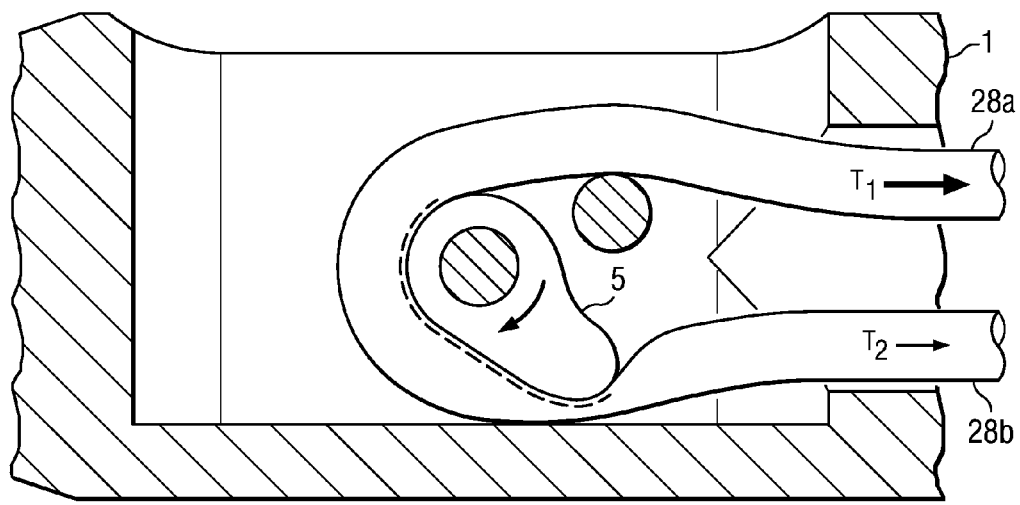

This calculate-able portion of the free leg tension (T2) depends on the relative dimensions or distances of the perpendicular extensions 53, 63 to calculate relative moments about the axis 46. Shown here, torque arm 60 rotates so that the torque arm tip (surface) 64 may travel through aperture 44 so that a portion of the torque arm is at least partially disposed outside anchor outer surface 12 when in the locked position. Aperture 44 may allow torque arm 60 to have increased dimension relative to free arm 50 without interfering with the inner wall of the chamber 47. This may add a further suture locking area (not shown here), as torque arm tip 64 may then wedge suture 28 against the inner wall of the bone or tissue that the anchor 10 is imbedded within. Differing from the embodiment described in FIGS. 1A and 1B, a torque arm 60 (preferably having a relatively larger dimension than the opposed locking arm 50) may allow cam 42 to be preferably formed from a low friction material, as torque rather than friction is the significant generator of the cam 42 motion and the ability of cam 42 to wedge the suture 28 against the inner wall of chamber 47.

The clamping or wedging force of the locking arm 50 against the lumen 24 may depend on the relative extensions of the locking arm 53 and torque arm 63 as well as the angles α and β and axis 46. In general, elongate arms 50, 60 extend radially from axis 46 and are approximately substantially opposed to each other, for example, in certain embodiments the locking arm 50 is disposed on the opposite side of the cam axis 46 as compared to the torque arm 60, and may be at least 130 degrees relative to each other, measured in any direction.

Anchor Implantation Using Instrument

Figure 4A:
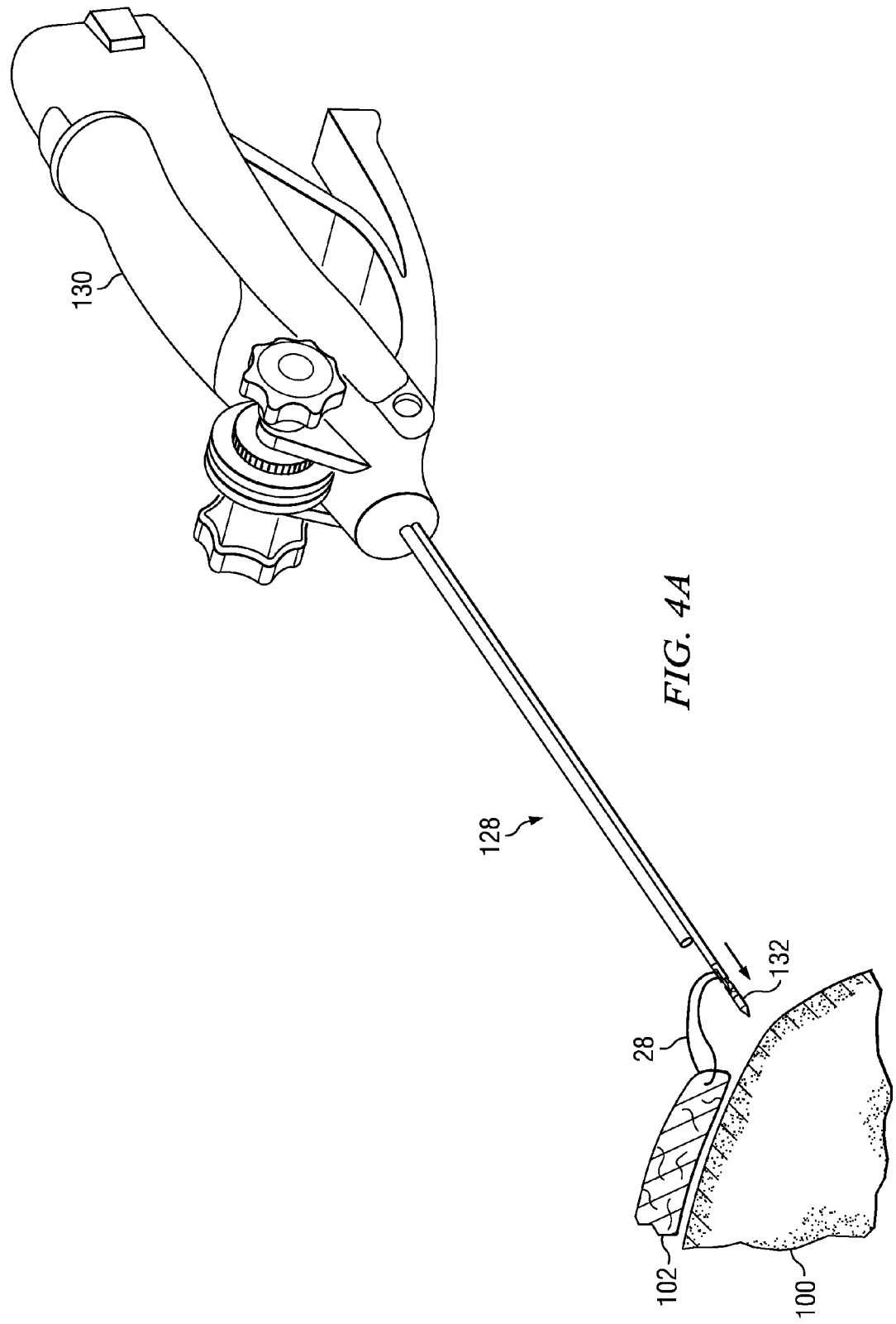
FIGS. 4A, 4B and 4C show a representation of a method of inserting and anchoring the suture anchor according to at least certain embodiments in the present disclosure.

Now turning to FIG. 4A, an example is provided for illustrating anchor implantation. An instrument and method similar to that described in U.S. Patent Application Publication No. 2009/0069823 (incorporated by reference herein) may be used to insert anchor 132, located at distal end of insertion instrument 128. As shown, suture 28 may be previously stitched, connected to or looped through tissue 102 and pre-assembled within anchor 132 and instrument 128. The stitching process may be accomplished by any known means, and any known suture stitch may be employed. A stitch is desirably secured so that the suture is not inadvertently separated from the tendon after completion of the repair procedure, necessitating re-entry to the surgical site. In preferred approaches, the suture is attached to the soft tissue using a "mattress stitch," which is well known in the art as being a particularly secure stitch which is unlikely to fail postoperatively.

Figure 4B:
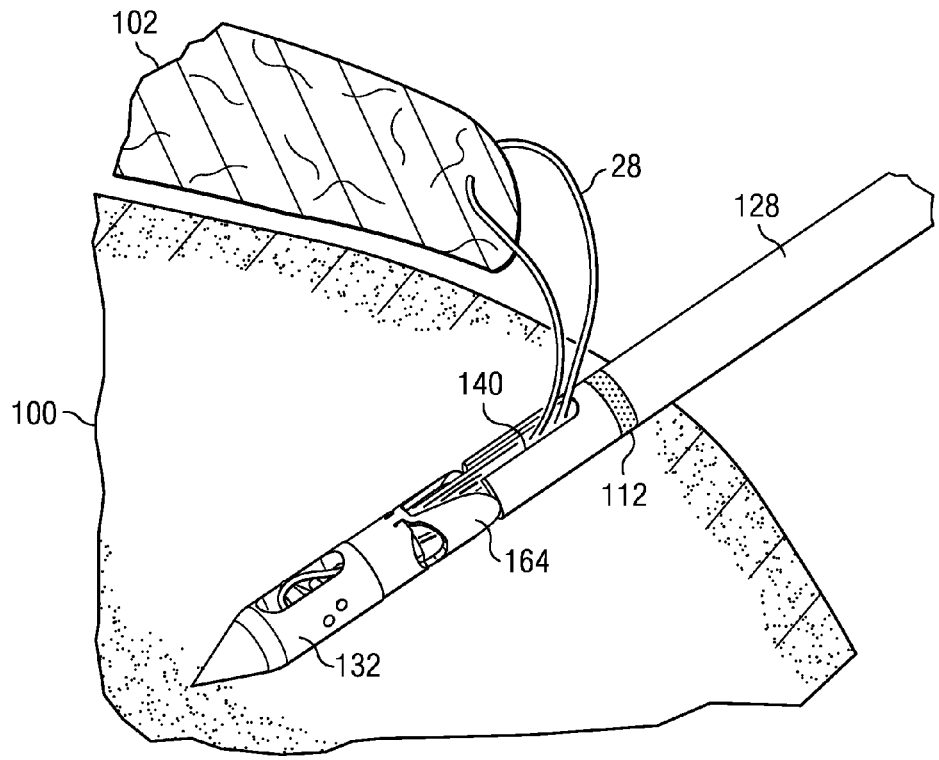

Anchor 132 may then be brought into contact against the underlying bone region 100 using instrument handle 130. In alternative methods of implanting and utilizing anchor 132, anchor 132 may be inserted by instrument 128 through a first portion of the soft tissue 102 to be repaired and then brought into contact against the underlying bone region 100, as is described in more detail in U.S. Patent Application Publication No. 2009/0069823. Now referencing FIG. 4B, with the piercing tip of anchor 132 contacting the bone 100, the proximal end of the instrument 128 or handle 130 may be tapped, e.g., by using a mallet, to drive the suture anchor 132 into the bone at a depth of, for example, approximately 6 mm. If viewed through an arthroscope, primary anchor 132 may be driven into the underlying bone 100 until an anchor depth indicator 112, e.g., a colored marking or gradation is visible just above or at the bone 100 as a visual indicator to the user that the appropriate depth for anchor insertion has been reached. This may indicate that the anchor wings 164 have been inserted at the correct depth. Instrument 128 may also have lateral aperture or opening 140, located at the distal portion of the instrument but proximal to anchor wings 164, operable to allow passage of suture 128 from tissue 102 into the anchor. Suture 28 may then extend distally from aperture 140 within anchor 132, around a cam (not shown) and return proximally within instrument (not shown here) and may connect with a portion of the instrument handle 130, operable for managing the suture 28 during insertion and tensioning.

Figure 4C:
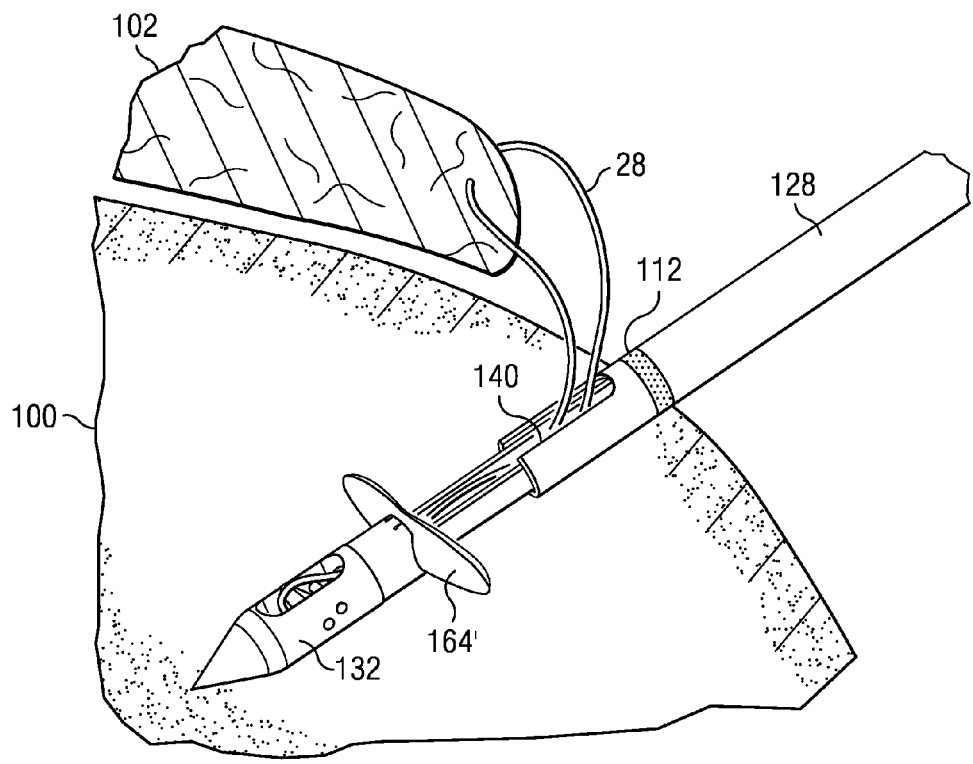

With suture anchor 132 suitably implanted, the anchor wings 164' may be deployed within the bone 100 using instrument 128, to lock the position of anchor 132 and to prevent or inhibit anchor 132 from being pulled out of bone 100, as shown in FIG. 4C.

Anchor 132 may then be released from instrument 128, which may be achieved by a variety of mechanical means, operable to have a weakness or failure point that fractures or disconnects upon application of a force or torque. Some methods for this release are described in U.S. Pat. No. 6,585, 730, which is hereby incorporated by reference herein. Also, it is to be understood that a wide variety of structures may be included with the suture anchor to implant the anchor in bone including without limitation barbs, ridges, threads, etc. Aspects of an instrument and method described in U.S. Patent Application Publication No. 2009/0069823 (which is hereby incorporated by reference in its entirety) may be used to insert and deploy anchor 132. Additionally, the anchor may be implanted in other manners, and without a sophisticated instrument as described above.

Figure 5A:
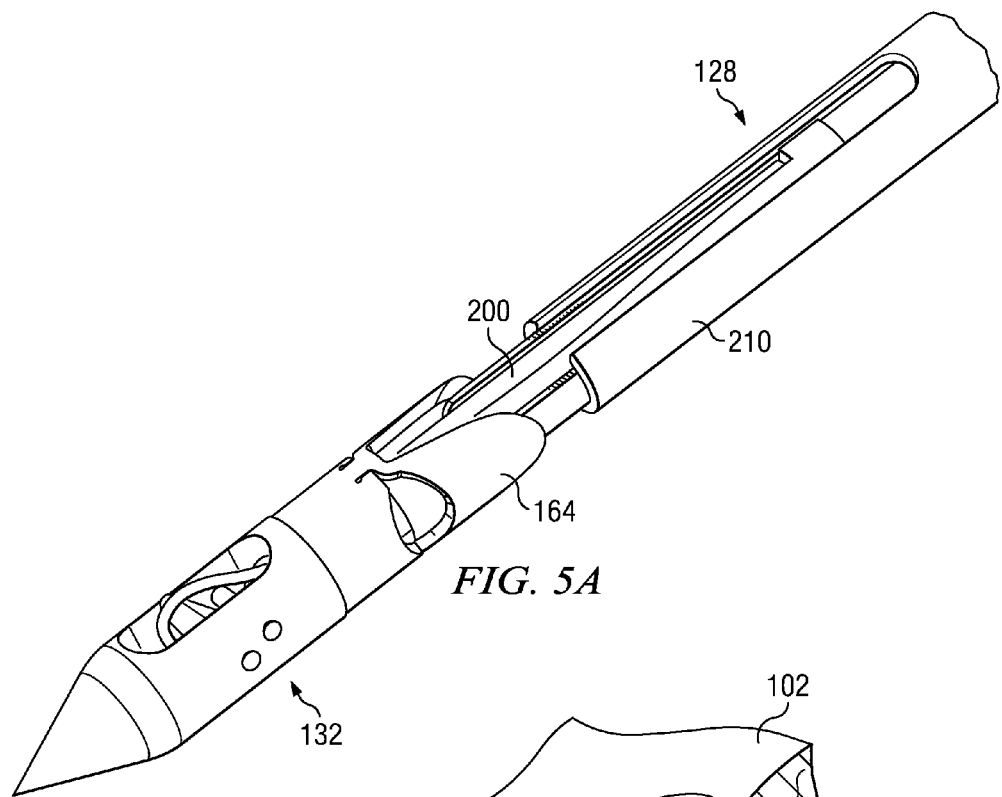
FIG. 5A illustrates a suture anchor deployment method.
Figure 5B:
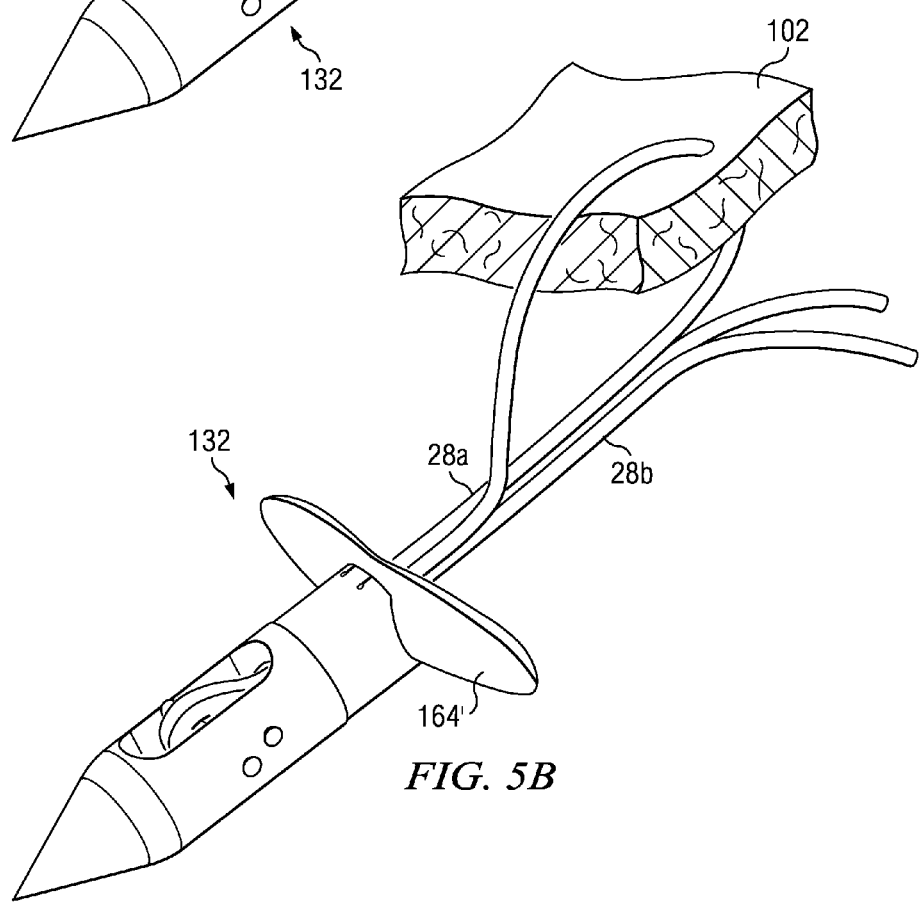
FIG. 5B illustrates a suture anchor with the anchoring structure deployed and the suture connected with tissue, according to at least certain embodiments in the present disclosure.

FIG. 5A shows one embodiment of instrument distal end that may be used to deploy or activate anchoring structure, and is described in more detail in U.S. Patent Application Publication No. 2010/0191283, hereby incorporated by reference herein. Instrument 128 includes a shaft 200, die or driver 210 that moves relative to the anchoring structure 164 so as to urge the anchoring structure radially outwards. FIG. 5B shows a deployed anchoring structure 164' with the bone passage or target bone tissue removed for clarity. Suture 28a is stitched in a suitable manner to a portion of soft tissue 102, such as a tendon, which is to be secured to a bone (not shown). Suture 28 then extends distally through anchor lumen around cam (not shown) and then returns proximally so as to leave a free end 28b. The free end 28b may extend within instrument (not shown) to manage the suture free end 28b during anchor 132 insertion and deployment.

Figure 6A:
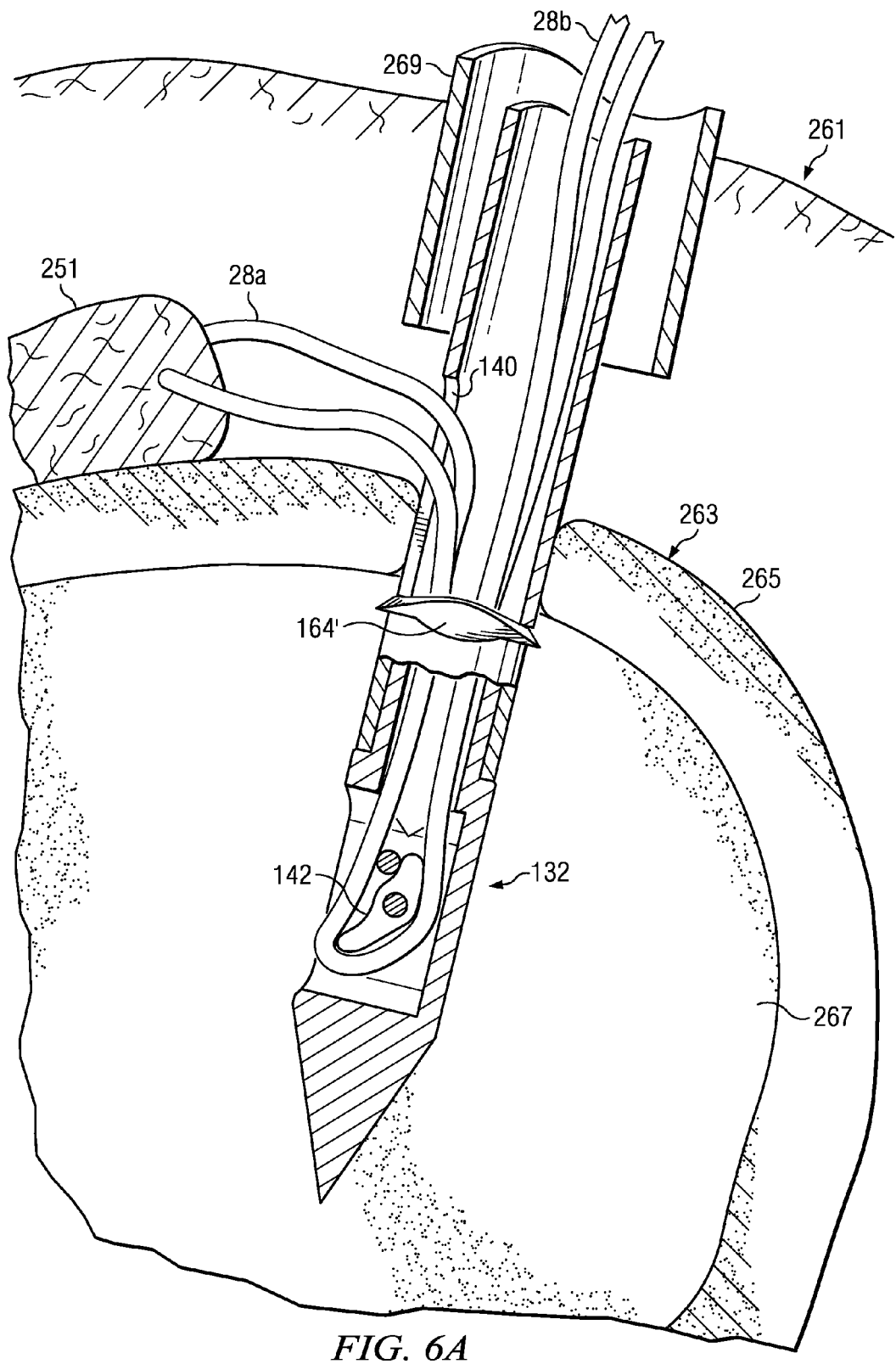
FIGS. 6A and 6B illustrate a method of using a suture anchor in rotator cuff tissue according to at least certain embodiments in the present disclosure.

FIG. 6A shows a cross section of anchor 132 similar to the anchor described in FIGS. 2 and 3, or alternative embodiments to be described in later figures. Anchor 132 is shown within bone tissue 267, possibly a rotator cuff, and with anchoring structure 164' deployed in the bone. Thus, there is shown in FIG. 6A a shoulder 261, which comprises a humeral head 263, including an outer cortical bone layer 265, which is hard, and inner cancellous bone 267, which is relatively soft. As is typically the case for rotator cuff injuries, in this instance the supraspinatus tendon 251 has become separated from the humeral head 263, and an objective of the rotator cuff repair procedure is to reattach the tendon 251 to the humeral head 263. Alternate rotator cuff repair procedures are also discussed in U.S. Pat. No. 6,524,317, and entitled "Method and Apparatus for Attaching Connective Tissues to Bone Using a Knotless Suture Anchoring Device", which is herein expressly incorporated by reference.

To effect the rotator cuff repair, the practitioner may first create an incision in the patient's shoulder 261, into which may be inserted a trocar 269, as shown in FIG. 6A. The trocar 269 permits access to the procedural site for visualization instruments, as well as working instruments, and permits the procedure to be completed arthroscopically. Anchor 132 may then be connected with suture 28 and then inserted according to methods described earlier. Insertion to the cortical layer 267 is important to ensure anchoring structure 164' gains good purchase on the bone. FIG. 6A shows anchoring structure 164' deployed, at which point the deployment instrument may be disconnected from the anchor 132 as discussed earlier and removed from the site.

Figure 6B:
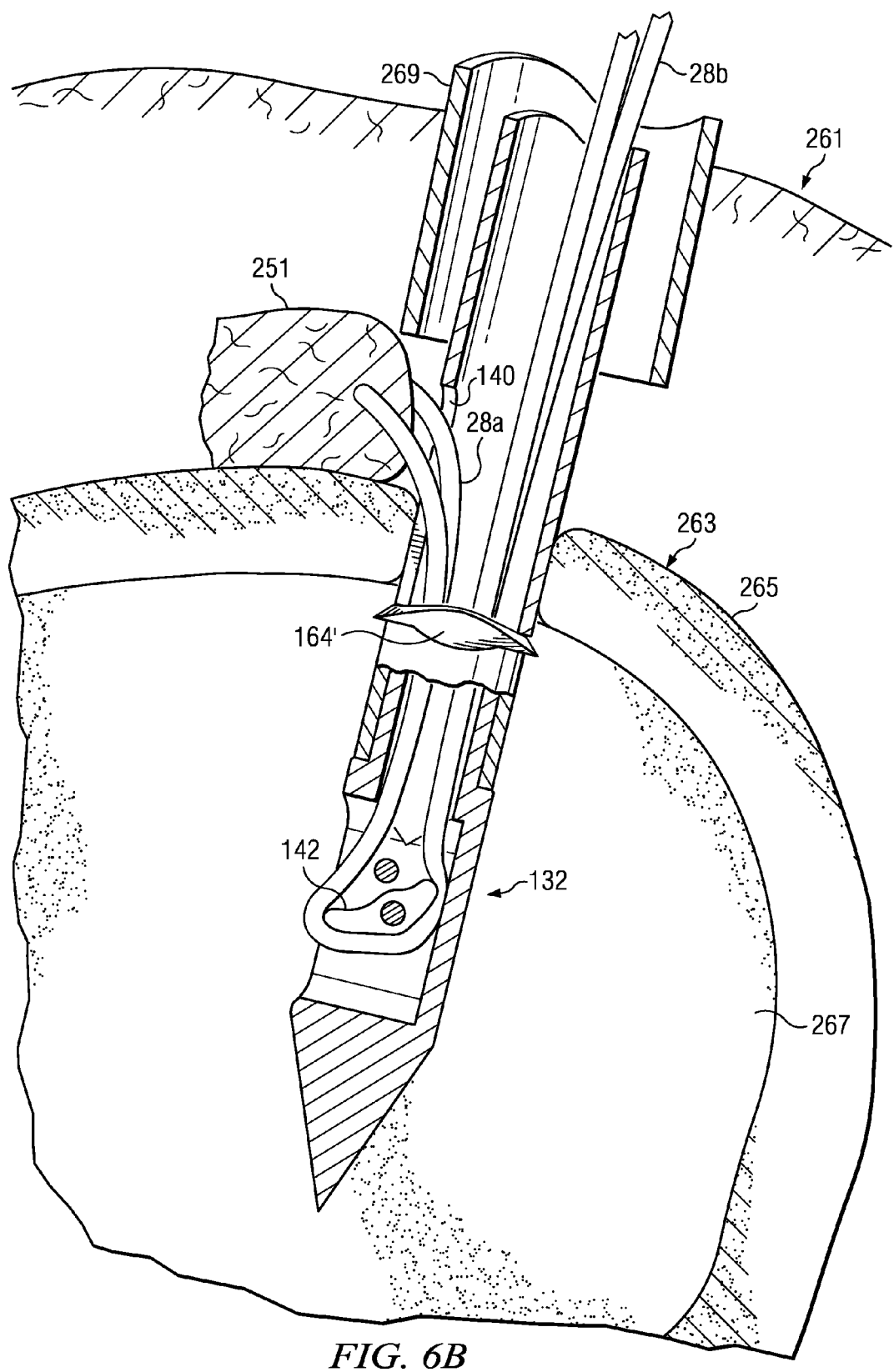

Suture locking member or cam 142 is shown in an open position, meaning that the suture free end 28b may be freely tensioned or withdrawn proximally to draw tissue 251 to the correct location for reattachment to the bone. As discussed supra, the bound leg or legs 28a of the suture have been connected with the tissue or tendon 251 and may extend through a lateral aperture 140 in the delivery instrument 128 to gain access to the suture anchor 132, about the cam 142, until such time as the tendon 251 binding in the bound leg 28a of the suture 28 creates a tension in the suture 28. This will occur when the tendon 251 has been drawn toward the anchor 132 as shown in FIG. 6B, and is itself under appropriate tension for an anatomically proper repair and otherwise snugly situated with respect thereto. Non-limiting examples of threshold distances between the tissue 251 and the proximal end of the anchor range from 2-8 mm and more preferably 3-6 mm. The suture may be drawn by hand, by instrument, or a combination thereof.

Once the tension on the bound limb 28a is present, the practitioner may release or otherwise adjust the tension on the free limb 28b so as to allow the tension in the suture bound leg 28a to rotate the suture locking member 142 to the locked position, as is shown in FIG. 6B.

Reversibility

The suture locking member described herein may be unlocked. It is reversible. Retensioning may be possible to permit the continued adjustability of the bound end 28a by applying tensile force to the free end 28b of the suture. This is useful as a surgeon will often find that, during the course of a procedure, after the tendon/soft tissue 251 has been brought into what is believed to be a desired position relative to the bone to which it is being secured, and the suture 28 has been locked into place to retain the tendon in that orientation, a further adjustment is necessary or desired to optimize the outcome.

By way of further example, after the free end 28b has been pulled proximally, as described in FIGS. 2 and 3, sufficiently that a tension is created in the bound end 28a (due to approximation of the tendon 251 to the bone 263), and the suture 28 has been locked by the cam 142, the bound end 28a is anchored in a fixed position. This ensures that the tendon is not movable relative to the bone after completion of the procedure. On the other hand, if the practitioner requires, the cam may be unlocked by applying sufficient tension on the free end 28b, (possibly also in combination with releasing tension on the bound legs 28a) so as to permit adjustment of the size of the suture loop through the tendon 251, which in turn permits adjustment or fine tuning of the position of the tendon 251 with respect to the bone. The practitioner may make these adjustments by hand or using an instrument. Once the tendon 251 is in the desired location, the suture 28 may then be considered locked and the free end 28b may be trimmed near the proximal end of the anchor portion 164', and the incision is closed. The free end 28b may be cut off after all final adjustments have been made, as discussed above, so that the tendon is precisely positioned as desired.

Alternative Embodiments

FIGS. 7-9 show alternative embodiments of a suture anchor with a cam-like suture locking mechanism. These embodiments are similar in spirit to the suture anchor described in FIGS. 2 and 3 and may generally have a smooth outer surface for smooth insertion, and may be tubular in general shape with flat surfaces for easier manufacture. Generally alternative embodiments may have an anchoring portion that engages with the target tissue and becomes locked in the wall of the bone passage (not shown) using a variety of anchoring means such as barbs, threads, expansion ribs, molybolts, rivets, and other mechanisms. Some embodiments of anchor may include deformable wings that may be permanently or reversibly deformed to have a larger profile and anchor or fix a suture anchor within the bone passage. Anchor distal end may comprise a piercing tip configured to pierce soft tissue and be driven into and through bone. Accordingly, the anchors may be fabricated from a metal such as 316L stainless steel, although other materials such as titanium may be used. Alternative configurations may include a blunted tip or threaded tip for inserting into a prepared bone passage.

FIG. 7A shows a cross sectional isometric view of an anchor 700 with a cam portion 701 having a locking surface 715 in an alternative location compared with some other embodiments described herein. The cam portion 701 in this embodiment may include a shelf or surface 715 located towards the distal portion of cam portion 701. This shelf 715 is operable as a surface for the locking arm 712 to wedge the suture (not shown here). Such an embodiment may have two apertures 716 and 717 to allow sufficient rotation of the cam 712 to reach locking surface 715. Cam 712 also has an alternative shape which may allow anchor 700 to be smaller in size relative to some other embodiments and more evenly distribute the locking loads on the anchor 700.

FIGS. 8A and 8B show an alternative embodiment for a suture anchor 800 with a flexible pin suture cam 801. Anchor 800 is similar in spirit to previously described anchors with a proximal anchoring portion 805 and lumen opening 806 to provide a path for the suture 28 to extend distally through and gain access to a flexible suture cam 801, operable to lock suture 28 in position. In this embodiment, a distal portion of anchor 810 may be preferably manufactured from a more flexible material, such as a biocompatible polymer, so that the complex shapes, including the cam 801 may be readily molded as one piece.

However, as mentioned above, the materials, components and shapes of the suture anchor of the present invention may vary widely. The suture locking member may take a wide variety of shapes including without limitation a cam, wedge, rocker, kidney, arcuate, and plate. Example materials include without limitation steel and biocompatible polymers. Example manufacturing techniques include without limitation machining and injection molding.

In the embodiment shown in FIGS. 8A and 8B distal tip 815 and cam 801 may be part of distal portion 810. Cam 801 may be molded so that locking arm 803 has a neutral position that allows for easy suture 28 movement axially within anchor 800, so that the suture 28 is free to move and draw tissue to the desired location. However locking arm 803 is connected with torque arm 804, via a living hinge 808. This living hinge 808 is operable to provide a pivot point for the cam 803, but does not rotate freely in the fashion described in certain embodiments described above, but rather twists or torques to become deformed to rotate locking arm 803 in a substantial distal direction. Torque arm 804 may be larger in dimension or perpendicular dimension, relative to locking arm 803, similar to those arms described in previous embodiment and once the suture bound leg 28a is under some tension T1, torque arm 804 may flex in a generally proximal direction, twisting or distorting hinge 808 so as to transfer some of this rotation to the locking arm 803 and wedge suture free end 28b within anchor 800. In one embodiment, living hinge is elastically or resiliently deformable so that it may return to its original state (substantially unchanged) when tension on the arms is removed. In this manner, the suture anchor may be locked, and unlocked and retensioned or adjusted, and then relocked without sacrificing strength or tightness of the ultimate suture lock.

FIG. 9 shows a cross section of another embodiment of a suture anchor 900. Anchor 900 is similar to the embodiment described in FIG. 2; however in this embodiment, suture locking member 910 has a pin 912 that enables locking member 910 to rotate about pin 912. Pin 912 may also slide within a slot 913. Slot 913 is located on a lateral side of anchor 900 and is sized so that pin 912 may slide along slot 913 freely. Consequently, cam member 910 can move in multiple directions and has multiple degrees of freedom. Use of a slot may allow suture 28 to be more easily routed and may also relieve some manufacturing tolerance requirements during production. Additional suture anchor designs having suture locking members with multiple degrees of freedom are described in U.S. Ser. No. 13/359,642, filed Jan. 27, 2012, and entitled "Free Floating Wedge Suture Anchor for Soft Tissue Repair" and U.S. Ser. No. 13/359,673, filed Jan. 27, 2012, and entitled "Restricted Wedge Suture Anchor and Method for Soft Tissue Repair".

Methods for Tissue Repair

Figure 10:
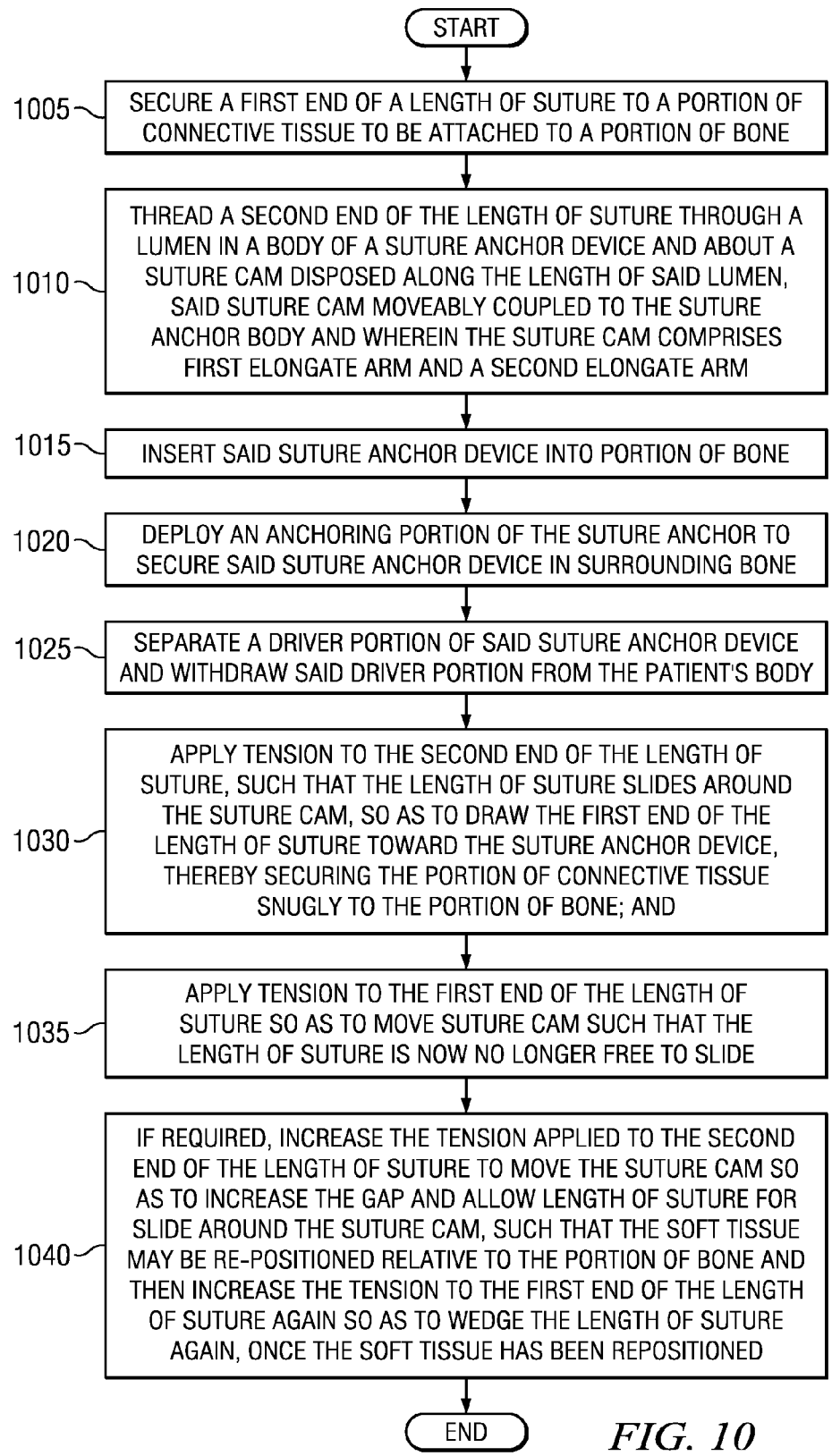
FIG. 10 shows a flow diagram of a procedure to secure connective tissue to bone according to at least certain embodiments in the present disclosure.

FIG. 10 is a flowchart representing a medical procedure for securing connective tissue to bone. The procedure includes the steps of securing a first limb of a length of suture to a portion of connective tissue to be attached to a portion of bone, using any method deemed suitable to the clinician (1005), followed by threading a second limb of the length of suture through a lumen in a body of a suture anchor device and about a suture locking member or cam disposed along the length of the lumen (1010). The suture cam member is moveably coupled to the suture anchor body and the suture cam comprises a first elongate arm and a second elongate arm, wherein the first arm may be substantially opposed to the second arm. The suture anchor device may be temporarily attached to an insertion instrument shaft distal end, having an opening to provide a passage for the length of suture to gain access to the suture anchor device as described in previous figures. The shaft distal end may also have a driver to deploy an anchoring element, disposed at the proximal end of the anchoring device. The suture anchor may then be inserted (1015) into a portion of bone, deep enough so that the anchor device proximal end is in the cancellous bone region. A marker or indicator may be present on the shaft distal end to aid in proper anchor placement. The anchoring portion or anchoring element may then be deployed (1020) to secure the suture anchor device in surrounding bone and then the driver portion may be separated (1025) from the suture anchor and withdrawn from the patient's body. Tension may then be applied (1030) to the second limb of the length of suture, such that the length of suture slides around the suture cam and through a gap disposed between a second elongate arm and a wall in the lumen, so as to draw the first limb of the length of suture toward the suture anchor device, thereby drawing the connective tissue closer to the anchor thereby securing the portion of connective tissue snugly to the portion of bone.

Tension may then be applied (1035) to the first limb of the length of suture, so as to move suture cam to reduce the gap such that the length of suture is now no longer free to slide. This tension to the first limb may be passively applied, as the tissue may resist any further motion as it abuts the bone. Alternatively this tension may be applied by the clinician. This step may be carried out by modifying the tension on the second limb (e.g., pausing, adjusting, or releasing tension on the free limb) so as to allow the tension on the tissue bound end to move the suture cam member. In embodiments, the movement of the suture locking member rotates thereby compressing the suture at a first contact location between the suture locking member and the anchor body.

Should the connective tissue need to be relocated, tension may be increased to the second length of suture, sufficient enough to move the suture cam so as to increase the gap and allow the length of suture to slide around the suture cam, such that the soft tissue may be re-positioned relative to the portion of bone. After the connective tissue has been relocated, the tension may then be increased to the first limb of the length of suture again, so as to wedge the length of suture again. The insertion instrument may then be removed from the area.

Figure 11:
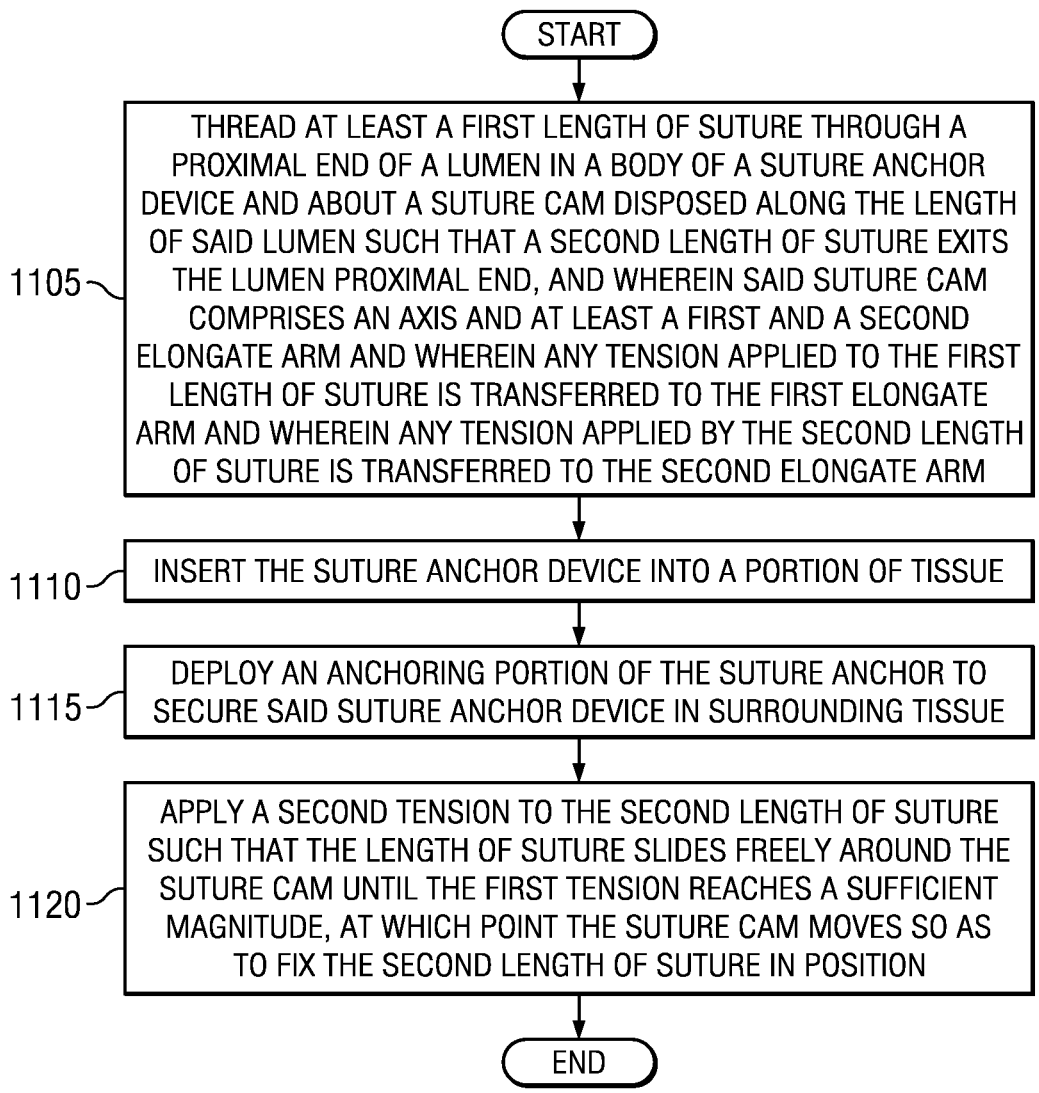
FIG. 11 shows a flow diagram of a method for operating a knotless suture anchor according to at least certain embodiments in the present disclosure.

FIG. 11 is a flowchart representing a method for operating a knotless suture anchor, comprising the steps of threading (1105) at least a first length of suture through a proximal end of a lumen in a body of a suture anchor and about a suture cam disposed along the length of the lumen such that a second length of suture exits the lumen proximal end. The suture cam comprises an axis and at least a first and a second elongate arm and wherein any tension applied to the first length of suture is transferred to the first elongate arm and wherein any tension applied by the second length of suture is transferred to the second elongate arm. The suture anchor is then inserted (1110) into a portion of tissue and an anchoring portion of the suture anchor is deployed (1115) to secure the suture anchor in surrounding tissue. A second tension is then applied (1120) to the second length of suture such that the length of suture slides freely around the suture cam until the first tension reaches a sufficient magnitude, at which point the suture cam moves so as to fix the second length of suture in position. The first tension magnitude may be reached through resistance from the tissue from any further movement, or from tension applied by the practitioner. The minimum first tension magnitude required to move the suture cam may be a proportion of the second tension, calculable by the relative dimensions of the first and second elongate arms and the resultant torque the first and second tensions apply to the cam.

In some embodiments, the suture may be fixed in position by wedging the second length of suture between the second elongate arm and an inside wall of the lumen. In some embodiments, the cam locking member may purely rotate, whereas in alternative embodiments, it may slide and rotate or bend and rotate.

Figure 12:
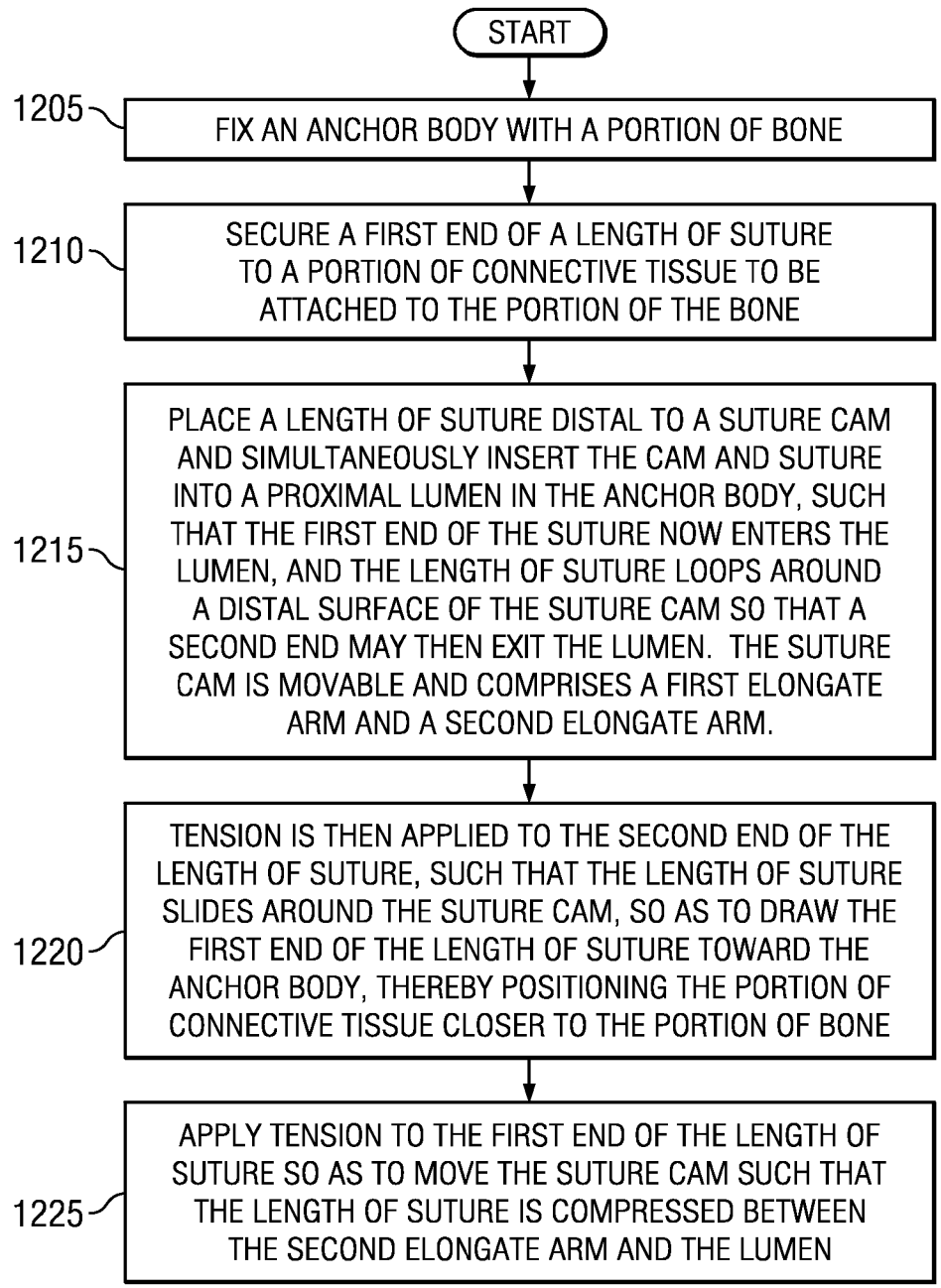
FIG. 12 shows a flow diagram of a procedure to secure connective tissue to a portion of bone according to at least certain embodiments in the present disclosure.

FIG. 12 is a flowchart representing a method of securing connective tissue to a portion of bone using a suture anchor device. The method includes fixing an anchor body within a portion of bone (1205).

A first limb of the length of suture is secured to a portion of connective tissue to be attached to the portion of the bone (1210).

The length of suture is then placed distal to a suture cam. The cam and suture may then be simultaneously inserted (1215) into a proximal lumen in the anchor body, such that the first limb of the suture now enters the lumen, and the length of suture loops around a distal surface of the suture cam so that a second limb may then exit the lumen. The suture cam is moveable and comprises a first elongate arm and a second elongate arm. Tension is then applied (1220) to the second limb of the length of suture, such that the length of suture slides around the suture cam, so as to draw the first limb of the length of suture toward the anchor body, thereby positioning the portion of connective tissue closer to the portion of bone; and tension may then be applied to the first limb of the length of suture (1225) so as to move the suture cam such that the length of suture is compressed between the second elongate arm and the lumen.

Figure 13:
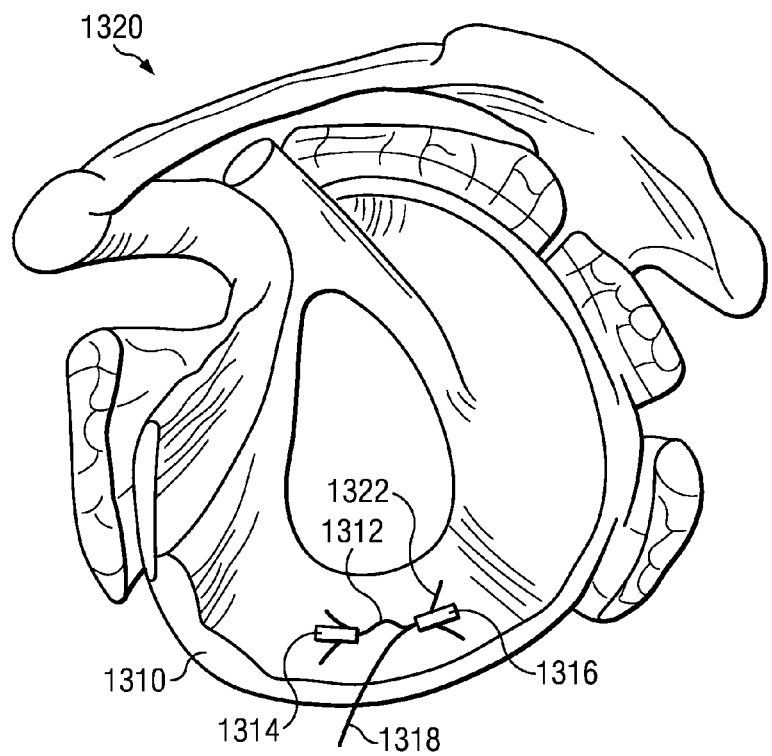
FIG. 13 is an illustration of a method for repairing a capsular tissue.

FIG. 13 illustrates a method for repairing capsular tissue. As shown, a glenoid section 1320 of a shoulder joint includes capsular tissue 1310. The capsular tissue 1310 serves to hold the humeral head in the shoulder joint. It should not be loose. However, if the capsular tissue is stretched (e.g., due to injury) the shoulder becomes loose. This is undesirable.

Repairing the capsule may be performed by stitching folds in the capsule to shrink its effective size (namely, plication). Tightening the capsule to the proper degree makes the shoulder more stable. Folds may be stitched in various manners. In one embodiment, and with reference to FIG. 13, a method comprises securing a first limb of a suture 1312 to a first anchor 1314.

A second limb of the suture 1312 is threaded or looped through a second anchor 1316. The anchors may have features similar to the anchors described herein. In the anchors shown in FIG. 13, radially deflectable members 1322 fix the anchor to the tissue.

Next, the first anchor 1314 and second anchor 1316 are placed in the tissue 1310 and connected with suture 1312. FIG. 13 shows the anchors separated by a region. Suture 1312 can be tightened incrementally by pulling on free suture limb or tail 1318. The amount of tension applied to the suture 1312 decreases the size of the region, tightening the capsule tissue 1310. This affects the stability and range of motion in the joint. The method thus allows the surgeon to increase tensions until a suitable stabilization is achieved that does not affect range of motion.

Figure 14:
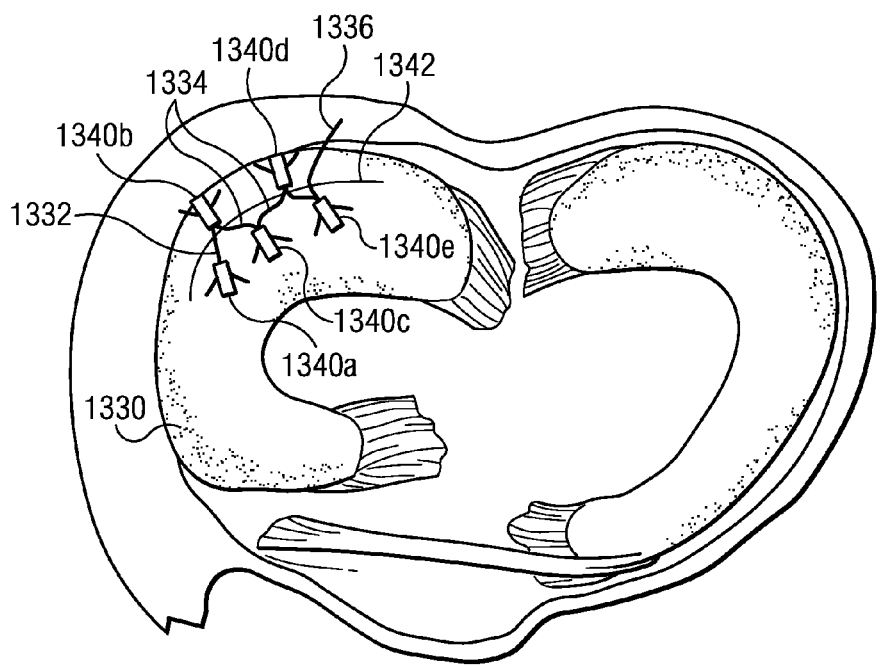
FIG. 14 is an illustration of a method for repairing a meniscus.

FIG. 14 illustrates another method for repairing soft tissue and in particular, a method for repairing a radial tear 1342 in the lateral meniscus 1330 of a knee.

Initially, the method comprises securing a first limb 1332 of a length of suture to a first anchor 1340a.

Next, the suture is looped or threaded through additional anchors 1340b, 1340c, 1340d, and 1340e such that a free suture limb 1336 extends from the last-threaded anchor. In the embodiment shown in FIG. 14, anchor 1340e is the last anchor of the sequence and free suture limb 1336 is shown extending therefrom. Although five anchors are shown in FIG. 14, the number may vary. In a preferred embodiment, the number of anchors placed ranges from 2-10. Generally, fewer anchors would preferably, but not necessarily, be deployed to close a smaller tear. More anchors (e.g., 6 or more) would preferably, but not necessarily, be deployed to close a larger tear.

Next, anchors 1340a,b, c, d, e are placed, one at a time, in the tissue such that the suture length extending between any two anchor bodies spans the tear. For example, anchor 1340b is next or adjacent in sequence to 1340a and the suture portion 1332 between the anchors 1340a and 1340b is shown spanning tear 1342.

Next, the physician pulls on the free suture limb 1336. This step places tension on the suture spanning the tear 1342, closing the tear so that it may heal.

Other modifications and variations can be made to the disclosed embodiments without departing from the subject invention. For example, numerous other methods for anchor deployment will be apparent to the skilled artisan. Moreover, the instruments and methods described herein may be utilized in other regions of the body (e.g., knee, hip, etc.) and for other tissue treatment procedures. Thus, while the exemplary embodiments have been described in detail, by way of example and for clarity of understanding, a variety of changes, adaptations, and modifications will be obvious to those of skill in the art. Therefore, the scope of the present invention is limited solely by the appended claims.

What is claimed is:

1. A suture anchor apparatus for anchoring a length of suture with respect to a target tissue, comprising:
   an anchor body comprising an anchoring structure for fixing the anchor body with respect to the target tissue, the anchor body further comprising an internal lumen;
   a suture locking member disposed at least partially within the internal lumen and wherein a portion of the length of suture is looped around the suture locking member such that a first limb and a second limb of suture exit the lumen; and wherein the suture locking member comprises a torque arm having a torque arm perpendicular extension and a locking arm having a locking arm perpendicular extension; and wherein a first tension on the first limb of suture is applied to the torque arm and a second tension on the second limb of suture is applied to the locking arm, and wherein the second tension allows the length of suture to slide around the suture locking member until the first tension is sufficient to move the suture locking member such that the length of suture is compressed between the locking arm and the anchor body and wherein the torque arm perpendicular extension is larger than the locking arm perpendicular extension.

2. The suture anchor apparatus of claim 1, wherein the length of suture is locked between the locking arm and a portion of the internal lumen.

3. The suture anchor apparatus of claim 2, wherein the suture locking member has an axis, and wherein the length of suture is compressed against a portion of the internal lumen that is on the opposite side of the axis to the torque arm.

4. The suture anchor apparatus of claim 1, wherein the suture locking member is moveable from a first position wherein said length of suture may freely travel across the suture locking member to a second position, wherein the locking arm prevents axial motion of said length of suture when in said second position.

5. The suture anchor apparatus of claim 4, wherein the torque arm and the locking arm are both elongate and terminate in a torque arm tip and a locking arm tip respectively, and wherein both arms extend radially from a suture locking member axis and wherein the torque arm perpendicular extension is defined between the suture locking member axis, and a center point of the torque arm tip in a direction perpendicular to an elongate axis of the anchor body and wherein the locking arm perpendicular extension is defined between the suture locking member axis, and a center point of the locking arm tip in a direction perpendicular to the anchor body elongate axis and wherein the torque arm perpendicular extension is significantly larger than the locking arm perpendicular extension when in both the first and second position.

6. The suture anchor apparatus of claim 5, wherein a portion of the torque arm tip extends outside of the anchor body when the length of suture is compressed between the locking arm and the anchor body configured so as to allow the torque arm perpendicular extension to be larger relative to the locking arm perpendicular extension and not be confined within the anchor body.

7. The suture anchor apparatus of claim 4, wherein the suture locking member rotates between the first position and the second position.

8. The suture anchor apparatus of claim 1, wherein a suture contact surface of the suture locking member comprises a low friction material and has a low friction surface texture.

9. The suture anchor apparatus of claim 1, further comprising a stop, disposed adjacent the suture locking member, wherein the stop limits the movement of the suture locking member via contact with a portion of the locking arm.

10. The suture anchor apparatus of claim 1, further comprising a distal piercing tip to pierce soft tissue and drive the suture anchor into bone tissue.

11. The suture anchor apparatus of claim 1, wherein the anchor body further comprises a threaded portion to threadingly engage bone tissue.

12. The suture anchor apparatus of claim 1, wherein the anchor body further comprises at least one bone lock component configured to retain the suture anchor in the target tissue.

13. A knotless suture anchor apparatus for fixing a length of suture with respect to a target tissue, comprising:

an anchor body having an anchoring structure for fixing the anchor body within the target tissue, and wherein the anchor body comprises an elongate axis and a proximal end with an opening configured for receiving a first portion of suture, the first portion of suture extending distally and around a suture locking member located within said opening, such that a second portion of suture then returns proximally through said opening; and wherein the suture locking member comprises a first arm and a second arm, wherein said first portion of suture is disposed such that a first tension on the first portion of the suture applies a first torque to the first arm and moves the suture locking member from an open position where the length of suture may freely slide around the suture locking member, to a locked position where the length of suture is locked between the second arm and the anchor body, and wherein the first arm extends further in a perpendicular direction relative to the elongate axis than the second arm in both the open and locked positions.

14. The suture anchor apparatus of claim 13, wherein a second tension may apply a second torque to the second arm and for equivalent first and second tensions, a resultant torque is generated by these first and second tensions on the suture locking member so as to move the suture locking member to the locked position.

15. The suture anchor apparatus of claim 13, wherein the length of suture is locked by compressing the second portion of suture between a lateral surface of the anchor body and the second arm.

16. The suture anchor apparatus of claim 13, wherein the length of suture is compressed against a lateral portion of an internal lumen of the anchor body.

17. The suture anchor apparatus of claim 13, wherein a second tension applies a second torque to the second arm, and wherein the first torque moves the suture locking member to the locked position at a lower first tension than the second tension.

18. The suture anchor apparatus of claim 13, wherein the suture locking member comprises a low friction material and has a low friction surface.

19. The suture anchor apparatus of claim 13, wherein the first portion of suture is configured to connect with tissue.

20. The suture anchor apparatus of claim 13, wherein said second portion of suture is in contact with said second arm and is operable to apply a second tension to the second arm and move the suture locking member from the locked position to the open position wherein the length of suture free to slide around the suture locking member.

21. The suture anchor apparatus of claim 13, wherein the anchoring structure for fixing the anchor body within the target tissue comprises a proximally disposed deformable anchoring element.

22. The suture anchor apparatus of claim 13, wherein the anchoring structure for fixing the anchor body within the target tissue comprises a threaded anchoring element.

23. The suture anchor apparatus of claim 13, further comprising a connecting member disposed between the suture locking member and the body.

24. A method for securing tissue with a suture anchor device, comprising:

manipulating a portion of a length of suture and a suture locking member such that a first length of suture extends into a lumen of the suture anchor device, around the suture locking member, and such that a second length of suture exits the lumen proximal end, and wherein said suture locking member comprises an axis and at least an elongate torque arm and an elongate locking arm; wherein the elongate torque arm is longer than the elongate locking arm; and wherein a first tension applied to the first length of suture is transferred to the elongate torque arm and wherein a second tension applied by the second length of suture is transferred to the elongate locking arm;

inserting said suture anchor device into a portion of tissue;

applying the second tension to the second length of suture such that the length of suture slides freely around the suture locking member until the second tension approximates the first tension; and releasing the second tension to the second length of suture whereby the first tension on the first length of suture moves the suture locking member so as to secure the second length of suture between the elongate locking arm and the lumen.

25. The method of claim 24 wherein the elongate locking arm and the elongate torque arm extend radially from the axis in substantially opposite directions to each other.

26. The method of claim 24, wherein the length of suture is secured by compressing the second length of suture between the elongate locking arm and a lumen side wall.

27. The method of claim 24, wherein the suture locking member moves by rotating.

28. The method of claim 27, wherein the suture locking member is a cam and rotates about a pin.

29. The method of claim 24, wherein the step of manipulating comprises placing the length of suture distal to the suture locking member and inserting said suture locking member into the lumen, while capturing the length of suture, such that the first length of suture enters the lumen and a second length of suture exits the lumen.

30. The method of claim 24, wherein the step of inserting the anchor device into a portion of tissue comprises rotating an externally threaded anchor body into bone tissue.

* * * * *